United States Patent
Dasgupta et al.

(10) Patent No.: US 7,582,482 B2
(45) Date of Patent: Sep. 1, 2009

(54) CONTINUOUS ION SPECIES REMOVAL DEVICE AND METHOD

(75) Inventors: Parnendu K. Dasgupta, Lubbock, TX (US); Petr Kuban, Lubbock, TX (US); Jordan M. Berg, Lubbock, TX (US)

(73) Assignee: Dionex Corporation, Sunnyvale, CA (US)

( * ) Notice: Subject to any disclaimer, the term of this patent is extended or adjusted under 35 U.S.C. 154(b) by 816 days.

(21) Appl. No.: 10/653,032

(22) Filed: Aug. 28, 2003

(65) Prior Publication Data
US 2005/0202563 A1    Sep. 15, 2005

Related U.S. Application Data

(60) Provisional application No. 60/407,920, filed on Sep. 3, 2002.

(51) Int. Cl.
| | |
|---|---|
| *G01N 35/08* | (2006.01) |
| *G01N 1/18* | (2006.01) |
| *B01D 15/08* | (2006.01) |
| *B01D 15/00* | (2006.01) |
| *B03B 5/00* | (2006.01) |
| *G01N 21/00* | (2006.01) |

(52) U.S. Cl. .................. 436/52; 436/150; 436/161; 436/178; 422/81; 422/82.03; 422/82.05; 422/82.07; 422/82.08; 210/198.1; 210/645; 210/656; 209/155; 209/208; 209/210

(58) Field of Classification Search .................. 436/52, 436/178; 250/299
See application file for complete search history.

(56) References Cited

U.S. PATENT DOCUMENTS

| | | | | |
|---|---|---|---|---|
| 4,510,058 A | * | 4/1985 | Cais et al. | 210/657 |
| 4,751,189 A | * | 6/1988 | Rocklin | 436/150 |
| 5,971,158 A | * | 10/1999 | Yager et al. | 209/155 |
| 6,153,393 A | * | 11/2000 | Seidel et al. | 435/7.1 |
| 6,297,061 B1 | | 10/2001 | Wu et al. | |

FOREIGN PATENT DOCUMENTS

WO    WO 02/23161 A1    3/2002

OTHER PUBLICATIONS

Boring, C.B., et al., "Compact, field-portable capillary ion chromatograph," *J. Chromatogr. A*, 804:45-54 (1998).
Dasgupta, P., et al., "Flow of Multiple Fluids in a Small Dimension," *Anal. Chem.*, 74(7):208A-213A (Apr. 2002).
Dasgupta, P., et al., "Suppressed Conductometric Capillary Eletrophoresis Separation Systems," *Anal. Chem.*, 65(8):1003-1011 (Apr. 1993).

(Continued)

*Primary Examiner*—Jill Warden
*Assistant Examiner*—Neil Turk
(74) *Attorney, Agent, or Firm*—Morgan, Lewis & Bockius LLP; David J. Brezner

(57) ABSTRACT

Apparatus and method for treating a liquid sample stream including at least one analyte ion species and matrix ion species of opposite charge to said one analyte ion species. The liquid sample stream flows through a treatment channel. A carrier liquid stream including a matrix ion species capture material flows substantially parallel to the sample stream in the treatment channel forms a liquid interface between them. The matrix ion species diffuses through the interface to contact and become bound by the capture material in said carrier liquid.

11 Claims, 16 Drawing Sheets

OTHER PUBLICATIONS

Foucault, A.P., et al., "Counter-current chromatography: instrumentation, solvent selection and some recent applications to natural product purification," *J. Chromatogr. A*, 808:3-22 (1998).

Kang, Q., et al., "An integrated micro ion-exchange separator and detector on a silicon wafer," *Chem. Eng. Sci.*, 56:3409-3420 (2001).

Kuban, P., et al., "Microscale continuous ion exchanger," *Anal. Chem.*, 74(21):5667-5675 (Sep. 2002).

Kuban, P., et al., "Vertically Stratified Flows in Microchannels. Computational Simulations and Applications to Solvent Extraction and Ion Exchange," *Anal. Chem.*, 75(14):3549-3556 (Jul. 2003).

Kutter, J., "Current developments in electrophoretic and chromatographic separation methods on microfabricated devices," *Trends Anal. Chem.*, 19(6):352-363 (2000).

Murrihy, J., et al., "Ion chromatography on-chip," *J. Chromatogr. A*, 924(1-2):233-238 (Jul. 2001).

Pyo, D., et al., "High Temperature Open Tubular Capillary Column Ion Chromatography," *Anal. Sci.*, 13(Supp.):185-190 (1997).

Rokushika, S., et al., "Micro Column Ion Chromatography with a Hollow Fibre Suppessor," *Chrom.*, 15:637-643 (1983).

Sjögren, A., et al., "Capillary Ion Chromatography with On-Line High-Pressure Electrodialytic NaOH Eluent Production and Gradient Generation," *Anal. Chem.*, 69(7):1385-1391 (Apr. 1997).

Small, H., et al., "Novel Ion Exchange Chromatographic Method Using Conductimetric Detection," *Anal. Chem.*, 47(11):1801-1809 (Sep. 1975).

* cited by examiner

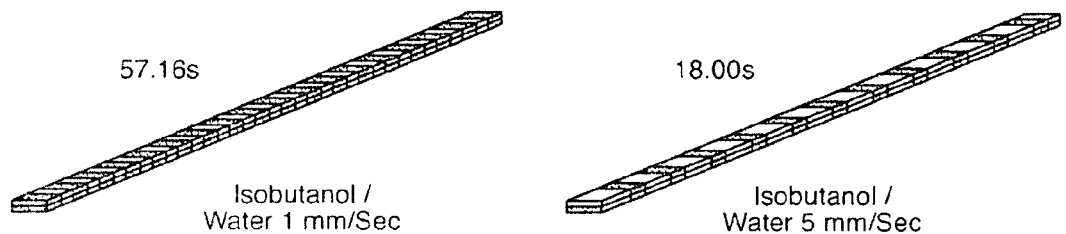
FIG. 9a — 57.16s Isobutanol / Water 1 mm/Sec
FIG. 9b — 18.00s Isobutanol / Water 5 mm/Sec
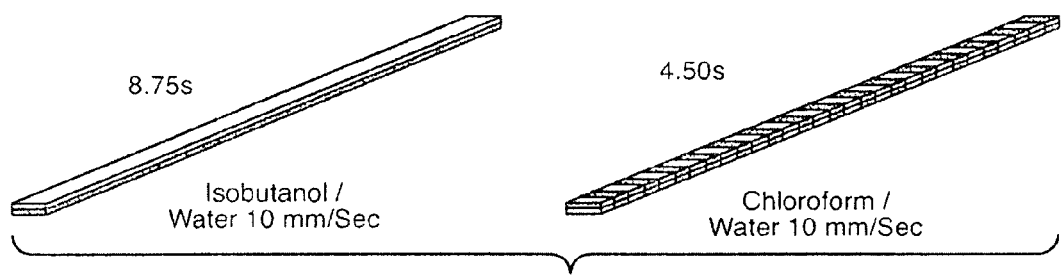
FIG. 9c — 8.75s Isobutanol / Water 10 mm/Sec ; 4.50s Chloroform / Water 10 mm/Sec
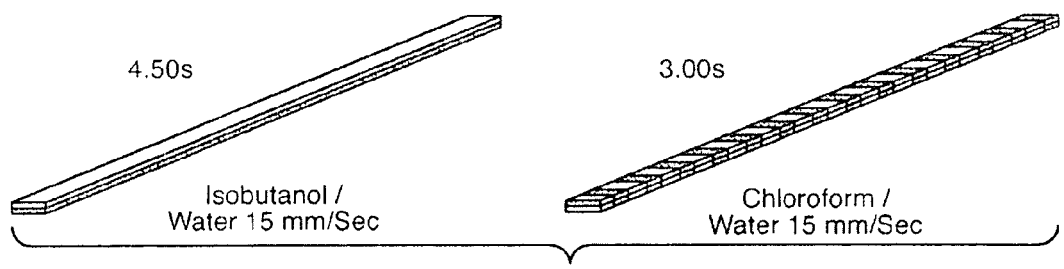
FIG. 9d — 4.50s Isobutanol / Water 15 mm/Sec ; 3.00s Chloroform / Water 15 mm/Sec
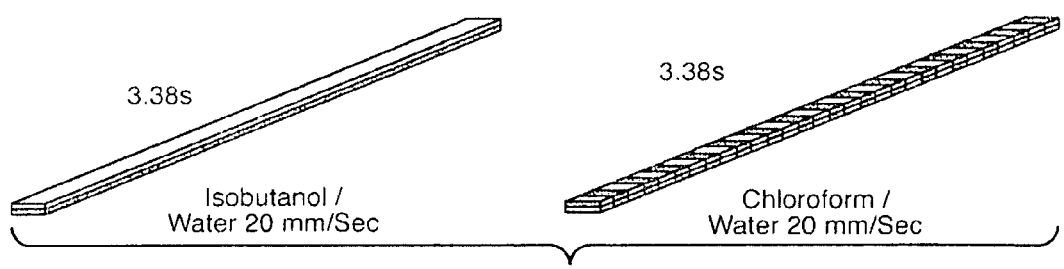
FIG. 9e — 3.38s Isobutanol / Water 20 mm/Sec ; 3.38s Chloroform / Water 20 mm/Sec
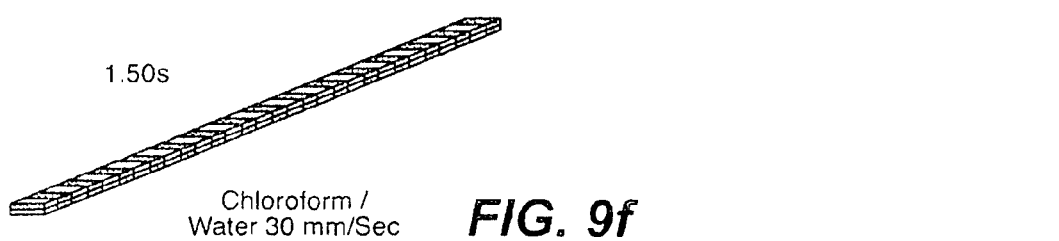
FIG. 9f — 1.50s Chloroform / Water 30 mm/Sec 5.75s Isobutanol / Water 10 mm/Sec 5.50s Isobutanol / Water 10 mm/Sec 2.25s High ST Isobutanol / Water 20 mm/Sec

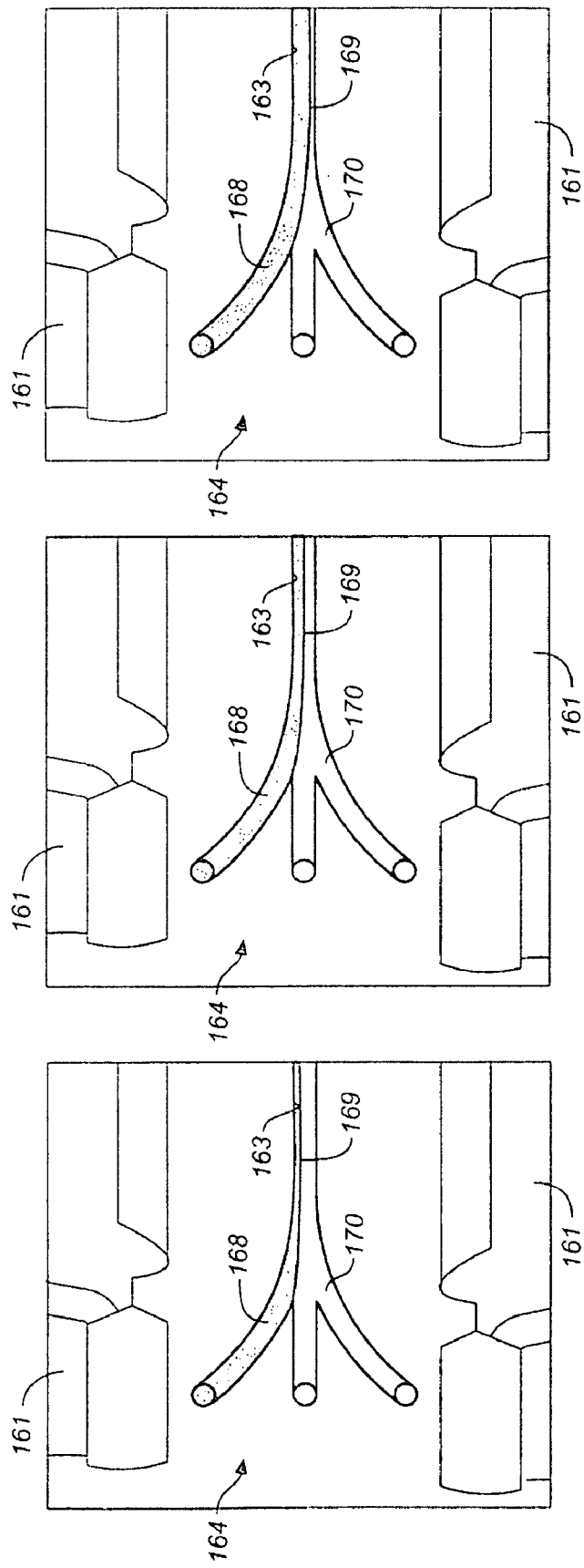

CONTINUOUS ION SPECIES REMOVAL DEVICE AND METHOD

CROSS-REFERENCE TO RELATED APPLICATION

This application claims the benefit of the filing date of U.S. provisional application Ser. No. 60/407,920 filed Sep. 3, 2002.

BACKGROUND

Since its introduction in 1975[1], suppressed conductometric Ion Chromatography (IC) has emerged as the preferred method for performing ionic analysis. The worldwide annual market today of IC equipment and related consumables is estimated to be of the order of US $200 million. There has been interest in carrying out IC in a miniature scale since the early years. As early as 1983, suppressed capillary IC was reported.[2] The entire system was not miniaturized. Subsequently, more refined versions of suppressed conductometric capillary IC instrumentation were presented, including a portable briefcase-sized unit.[3] The use of small tubular membrane-based continuous ion exchangers in these units is directly traceable to the earlier deployment of essentially identical devices for use in capillary electrophoresis (CE).[4] Other capillary-based efforts include internally latex-coated fused silica columns that could be used at elevated temperatures;[5] however, only optical detection was possible. More recently a similar system has been described in which separation takes place in a latex-coated channel microfabricated on silicon (as well as in non-negligible lengths of connecting tubing) with off-line optical detection.[6] Nevertheless, there is a belief, perhaps for good reasons,[7] that planar devices, however fabricated, are going to be the key devices of the future. In this view, Kang et al.[8] have described a multiple parallel channel microfabricated device for conducting IC. The stationary phase was prepared in situ and each channel contained its own dedicated conductivity detection electrodes. The limit of detection (LOD) of injected analytes was stated to be about 50 mM, which may have been well above the concentration (unspecified) of the biphthalate or carbonate eluent used. This performance level underscores the importance of the need to develop some means of carrying out continuous ion exchange based suppression for use in a planar format.

Synthetic polymer based ion exchange membranes have largely constituted the foundation of macro- and micro-scale conductivity suppression over the last two decades. However, it will be difficult to mass fabricate low-cost devices incorporating such membranes due to sealing and fabrication issues. This focuses on an alternative approach that relies on continuously flowing liquid membranes and draws on the recent teachings of Yager et al. and Kitamori et al. as detailed below.

SUMMARY OF THE INVENTION

In accordance with one embodiment of the present invention, apparatus is provided for treating a liquid sample stream including at least one analyte ion species and matrix ion species of opposite charge to said one analyte ion species. The apparatus includes a housing defining a flow-through treatment channel bounded by a liquid sample stream wall opposed from a spaced, generally parallel carrier liquid stream wall, said treatment channel including an inlet and an outlet, a source of said liquid sample stream in fluid communication with said treatment channel inlet, and a source of a carrier liquid stream including a matrix ion species capture material in fluid communication with said treatment channel inlet. The sample stream and carrier liquid stream are disposed in the treatment channel in substantially parallel flowing streams extending between the treatment channel inlet and outlet forming a liquid interface between said parallel streams, said matrix ion species being present at a substantially lower concentration in said sample stream at said treatment channel outlet than at said treatment channel inlet.

In another embodiment, a method is provided for treating a liquid sample stream including at least one analyte species ion and matrix ion species of opposite charge to said one analyte ion species. The method comprising flowing said sample stream from an inlet in a flow-through treatment channel to an outlet thereof, and flowing a carrier liquid stream including a matrix ion species capture material through said flow-through chamber. The sample stream and carrier liquid stream flow substantially parallel to each other in said treatment channel and forming a liquid interface between them. The matrix ion species in said sample stream diffuses through said interface to contact and become bound by said capture material in said carrier liquid so that the concentration of said matrix ion species at said outlet is at a substantially lower concentration than at said inlet.

In one embodiment, a method is provided for treating a liquid sample stream (preferably aqueous) including analyte ion species and matrix ion species of opposite charge to the analyte ion species. The aqueous stream flows through and out of a treatment chamber, usually without application of an electric field. Simultaneously, a carrier liquid stream flows in direct contact with the sample stream and includes a matrix ion species capture material with exchangeable ions of the same charge as the matrix ion species so that a portion of the matrix ion species are transported from the aqueous liquid stream to the capture material to be retained thereby to flow out of the treatment chamber in the carrier liquid.

In one embodiment, the capture material is an ion exchange material in liquid form. Preferably, for this embodiment, the carrier liquid stream is an organic liquid solvent for the liquid ion exchange material which is substantially immiscible with the aqueous liquid stream.

In another embodiment, a liquid capture material is capable of retaining the matrix ion species in ionic form or salt form by forming a salt or complexing with it.

In a further embodiment, the ion exchange material comprises a suspension of ion exchange particles in a carrier liquid which may or may not be immiscible in the aqueous sample stream.

In yet another embodiment, a compound is present in the carrier stream which reacts with the matrix ion species, or the molecule of the matrix ion species and its counter ion, to thereby remove substantially all of the matrix ion species in ionized form from the aqueous liquid stream.

As used herein, the term matrix ion species capture material will encompass at least all of the foregoing materials in the carrier stream flowing adjacent to and in contact with the aqueous liquid stream. Common to all of the foregoing mechanisms, in a preferred embodiment, a sufficient amount of portion of the matrix ion species in ionized form is removed from the aqueous liquid stream to accomplish suppression of the developing reagent as the term "suppression" is used in the ion chromatography field. Similar amounts or portions are removed when the treatment chamber is used.

BRIEF DESCRIPTION OF THE DRAWINGS

FIG. 9. Simulations of horizontally layered flows: left-butanol/water, right-chloroform/water. Linear flow rates (a)—1 mm.s$^{-1}$, (b)—5 mm.s$^{-1}$, (c)—10 mm.s$^{-1}$, (d)—15 min.s$^{-1}$, (e)—20 mm.s$^{-1}$, (f)—30 mm.s$^{-1}$.

FIGS. 16A-D. Experimental device. FIG. 16A illustrates the device with the channels filled with bromthymol blue in 10 mM NaOH solution for visualization.

FIGS. 16B-16D illustrate different ratios of the widths of the aqueous:organic phase within experimental device of FIG. 16A, in which FIG. 16B illustrates a ratio of 1:3, FIG. 16C a ratio of 1:1, and FIG. 16D a ratio of 3:1.

DETAILED DESCRIPTION OF THE PREFERRED EMBODIMENT

Figure 1:
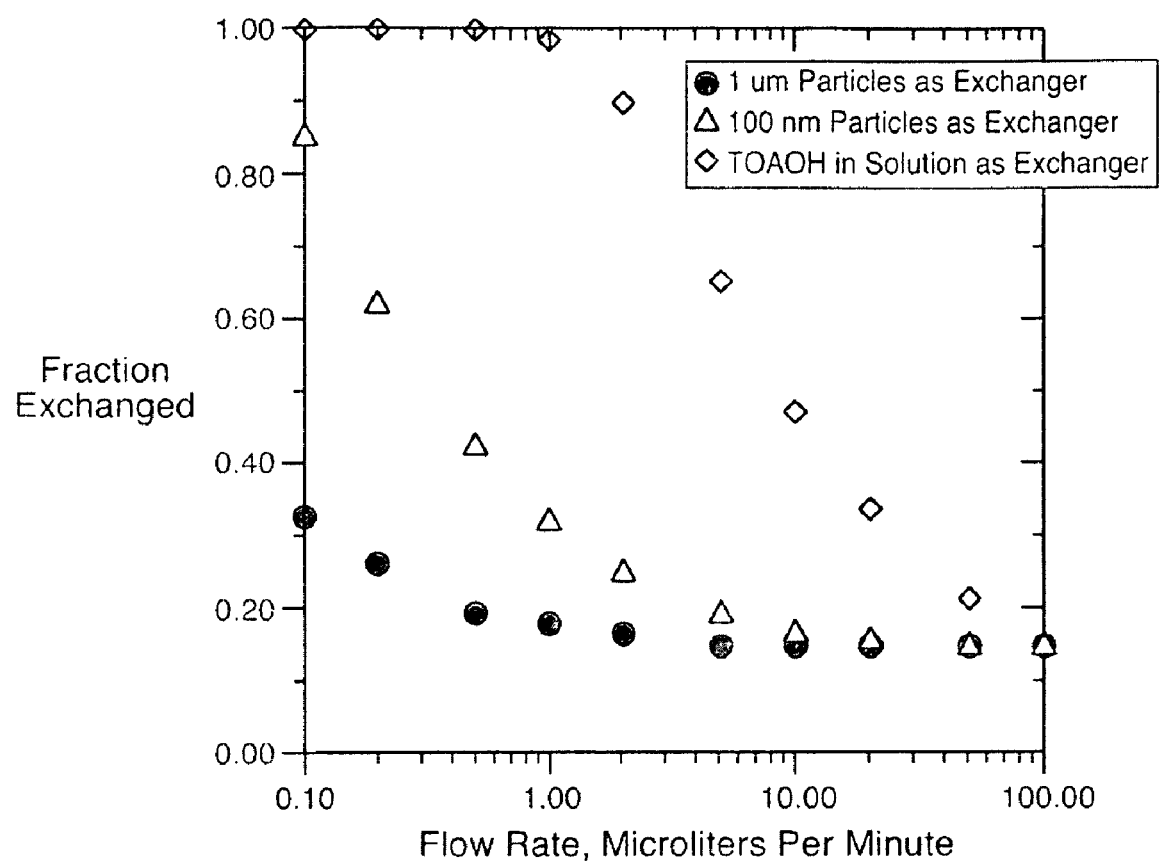
FIG. 1. Model computations. Efficiency of ion exchange for liquid ion exchanger and suspended ion exchange resin particles of different diameter.

Certain known principles applicable to many embodiments of the invention will be described.

In one embodiment, the present invention relates to a microscale continuous ion exchanger based on two liquid streams flowing in parallel. The ion exchange reaction occurs through diffusional transfer of molecules between the ion exchanger phase and the eluent phase and is applied for conductivity suppression. In one approach, a liquid ion exchanger (such as a strongly basic compound, e.g., tetraoctylammonium hydroxide, or a secondary amine, e.g., Amberlite LA-2) is dissolved in an organic solvent immiscible with the aqueous eluent. The system allows for sensitive suppressed conductivity detection of various inorganic cations. When a weakly basic secondary amine is used, conductometric detection of heavy metals is possible. In another approach, a suspension of finely ground ion exchange resin is used as the ion exchanger phase. In this case, the suspension need not involve an organic solvent. The potential of such a system as a chip-scale post-separation suppressor/reactor is evident.

When two fluids flow in parallel in a shallow flow path under conditions of low Reynold's number, the transfer of molecules/ions from one fluid to the other occur only by diffusion. Yager et al. described a microfluidic flow system of T or Y geometry where a sample stream and an indicator reagent stream enters through opposing arms of a T (or Y) and then flow side by side in a laminar fashion in the long arm. If the sample is a mixture of smaller analyte molecules and large macromolecules (or suspended cells), e.g., glucose in a whole blood sample, the smaller molecules, with a much larger diffusion coefficient than the large molecules/cells, will penetrate laterally into the indicator stream to a much greater extent. If a colored/fluorescent product is formed by the reaction of the analyte molecule and the indicator reagent (which may itself be a reagent immobilized on a particle), optically monitoring the product formed at a fixed spatial location will provide a measure of the analyte concentration.[9,10] Indeed, it has been demonstrated that diffusion coefficients can be measured this way.[11] Practical detection of human serum albumin that forms a red fluorescent product with a marker dye and fluorometric immunoassay of phenyloin in a blood sample diluted with labeled antigen were demonstrated.[12,13] If two input and two output channels are provided (i.e., the device is of H-geometry), it will in fact be possible to get an outlet stream that does not contain the low diffusivity moiety, i.e., cells, etc. Such a membraneless dialyzer or extraction device[14] is commercially available as the H-filter;[15] the underlying principles are not fundamentally different from the field flow fractionation teachings of Giddings.[16]

In their initial work, Sato et al.[17] used a Y-geometry microfluidic device as a flow injection platform where molecular diffusion was used to mix an analyte and a reagent under stopped flow conditions; the product was detected at μM concentrations by thermal lens absorptiometry. In subsequent work, these authors allowed an analyte to be extracted to an immiscible organic phase in a two-inlet, two outlet device (generally of a double-Y geometry with extraction taking place in the central connecting arm). Significant extraction of Cobalt-2-nitroso-5-dimethylaminophenol (Co-DMAP),[18] Ni-dimethylglyoxime[19] methyl red,[20] and an ion-pair involve a Fe (II) chelate,[21] etc. into an organic solvent were demonstrated. They also showed that the extraction of Co-DMAP was much more rapid when the sample stream to be extracted was flanked by extractant streams on either side using a device with three inlets and outlets.[22] Recently these authors presented ion sensing based on indicator ion-pair extraction aided by a neutral ionophore[23] and next, selective sequential extraction and measurement of $K^+$ and $Na^+$ by intermittent pumping of different ionophores[24] in the same microfluidic solvent extraction format.

When the treatment chamber is used as a suppressor in ion chromatography, matrix ion species in ionized or molecular form in the aqueous sample stream are removed so that the aqueous liquid stream leaving the treatment chamber is suppressed with respect to the matrix ion species as that form is used in ion chromatography. In this instance, the matrix ion species comprise the electrolyte developing reagent. Suppression generally means removal of a sufficient amount of electrolyte so that acceptably low background conductivity of the electrolyte in the sample stream would-flow through a conductivity detector.

Detection of the analyte ion species may be performed by any detector used for chromatography applications, including a conductivity detector. A fluid conduit transports the sample stream but not the carrier liquid stream from the treatment channel to the detector.

In another embodiment, treatment of the aqueous sample stream in the treatment chamber may take place before chromatographic separation to remove contaminants of opposite charge to the analyte ions which comprise the matrix ion species of the present invention. This application is referred to as pretreatment in a pretreatment device. The same principles apply for such pretreatment as for use of the treatment chamber as a suppressor between chromatographic separation and detection. Suppression in this instance will refer to similar reductions in the concentration of the contaminant matrix ion species. The present invention will be described in terms of using the treatment zone as a suppressor in an ion chromatography system.

Suppression Using Liquid Ion Exchange Materials

In this embodiment of the invention, an immiscible phase containing an ion exchanger of appropriate composition is used for carrying out continuous and near quantitative ion exchange for conducting suppression. As an eluent flows in parallel with an immiscible liquid bearing a dissolved (or suspended) ion exchanger, diffusive mixing and ion exchange will occur. If suspended ion exchanger particles are used, the carrier liquid bearing it may be miscible with the eluent.

In one embodiment, the matrix ion species capture material is a liquid ion exchanger dissolved in a carrier, preferably in a lipophilic (organic) liquid with low interfacial tension (e.g., less than $10 \times 10^{-3}$ N m$^{-1}$ and preferably less than $1.8 \times 10^{-3}$ N m$^{-1}$) and preferably substantially immiscible in water. Suitable organic carrier liquids include alcohols such as butanol, pentanol, hexanol, and benzyl alcohol, and possibly certain amines and amides and hydrolytically hindered esters.

Suitable liquid ion exchange materials contain an exchangeable ionic moiety that can be readily exchanged with the matrix ion species and which are retained in dissolved form in the carrier liquid and which holds the matrix ion species in the carrier liquid without back diffusion into the aqueous liquid. As described hereinafter, the mechanism of diffusion of the matrix ion species for ion exchange with the liquid ion exchange material is diffusion across the interface between aqueous phase and the substantially immiscible lipophilic or organic phase of the carrier liquid. For acid suppression, suitable ion exchange materials are substantially insoluble in water and highly soluble in the lipophilic carrier phase. Such materials include alkyl ammonium hydroxide and other quaternary, tertiary and secondary amines and their salts. Suitable ion exchange materials for base suppression include acids such as alkylsulfonic acid, alkylphosphonic acid, carboxylic acids, and other acids capable of ion exchange with cation matrix ion species and which are substantially insoluble in water and which are highly soluble in the lipophilic carrier liquid.

The liquid ion exchange material will be described in more detail. For conductivity suppression via continuous ion exchange in the liquid phase to work in the envisioned manner in a planar shallow channel, the following parameters should be considered. The separation system effluent (whether from a microscale IC or CE) is likely aqueous liquid stream. For liquid ion exchangers, the carrier for the ion exchangers preferably is an immiscible organic phase solvent that will flow in conjunction with the aqueous phase in the channels in the desired fashion Surface forces at the liquid-solid and liquid-liquid interfaces as well as the flow rate regime govern whether the two liquids flow as continuous phases, as desired, or break up into discontinuous segments. (The latter is also understandably promoted by surface irregularities.) Also, the ion exchanger should be easily soluble in the organic phase and insoluble in the aqueous phase. Of the organic solvents tested, hexane and xylene did not fully meet either criterion. Methylisobutylketone (MIBK), ethyl acetate and 1-butanol all formed well-defined continuous interfaces in conjunction with an aqueous stream flowing in parallel. Ethyl acetate was not suitable for the specific application, however, because present use involves dissolution of or contact with strong acids and bases. This leads to the hydrolysis of the ester, producing conductive acetate ions. Between the two remaining solvents, butanol proved to work better. Butanol easily dissolves the liquid ion exchangers described; it is also to be preferred in terms of toxicity and cost. However, the flow interface was not always stable with butanol. The addition of Triton X-100 to the butanolic phase was effective in eliminating this problem.

The Choice of a Liquid Ion Exchanger. Preferably, the liquid ion exchanger compound (matrix ion capture materials) should dissolve in the organic phase but its solubility in the aqueous phase should be limited. For anion exchangers we started with strongly basic tetraalkylammonium hydroxides, which are readily soluble in 1-butanol. However, the mutual solubility of butanol and water in each other is not negligible (0.4% butanol in water, 6% water in butanol) but they would be considered substantially immiscible for the present invention. If the organic cation is not sufficiently hydrophobic, there may be significant leaching to the aqueous phase. This was found to be the case for tetrabutylammonium and tetradecyltrimethylammonium ions. In contrast, TOAOH leached relatively little into water, except at high concentrations. Similarly, the secondary amine LA-2 also showed low leaching into the aqueous phase, as based on conductance measurement. Table 1 lists the specific conductance of an aqueous layer shaken with butanolic solutions of different potential chemical-suppression agents.

TABLE 1

Specific conductances of aqueous layers shaken with butanolic solutions of ion exchanger.

| Ion exchanger solution | Specific conductance of the aqueous layer |
|---|---|
| 150 mM TOAOH | 293 µS/cm |
| 15 mM TOAOH | 14.9 µS/cm |
| 10% Amberlite LA-2 | 17.8 µS/cm |
| 1% Amberlite LA-2 | 1.3 µS/cm |
| 100 mM DBSA | 3360 µS/cm |
| 100 mM HDSA | 4120 µS/cm |
| 100 mM ODSA | 2780 µS/cm |

Note that this degree of complete equilibration between an aqueous stream and the organic phase is not reached in the actual diffusion-based devices and the equilibrium "extracted" conductance values should be regarded as the limiting values for the "leached" conductance. Thus, much of our suppression work with eluent acids was done with TOAOH or Amberlite LA-2 as the anion exchanger.

Table 1 also shows that all strong acid type liquid ion exchanger acids tried (including octadecylsulfonic acid, the most hydrophobic of the acids tested) leached into the aqueous phase. As we found for benzoic acid, there are many carboxylic acids, which are essentially water-insoluble, but when a butanolic solution of such an acid reacts with an aqueous solution of an alkali hydroxide, the alkali metal carboxylate will partition significantly to water. An alternative is to use colloidal suspension of a cation exchange resin as described in a later section.

Model

In general, the aqueous liquid and carrier stream flow parallel to each other in direct contact in a liquid interface in the treatment zone of the chamber. Preferably, the liquids flow at a smooth, i.e., generally laminar (not turbulent) flow rate. For maximum efficiency, the width of the flow channel should be relatively narrow so that the outer boundary of the aqueous sample stream and carrier streams are close enough to the liquid interface to predict diffusion of the matrix ion species to contact matrix ion species capture material near the outer boundary of the channel. Suitably, the two streams flow side-by-side (formed "horizontally") or one on top of the other (formed "vertically"). In the latter instance, the carrier stream is preferably on the bottom, and so gravity can assist in maintaining separate streams for immiscible solvent carrier liquids. Suitable width dimensions for the side-by-side stream are less than 500 microns for the aqueous stream; no particular limitations exist for the carrier liquid, as long as a sufficient amount of reagent is available Similarly, suitable vertical dimensions for the vertically disposed aqueous stream are less than 500 microns and less than 500 microns for the carrier liquid stream. Generally, efficiency will increase with decreasing being related to the inverse of the square of the width of the channel (i.e., the distance away from the interface). The system will first be described with respect to the side-by-side streams and to the liquid ion exchange material.

By way of example, an HCl developing reagent is used for the analysis of cations such as $Na^+$ in NaCl. The carrier stream can be an organic phase of butanol with the liquid ion exchange material TOAOH dissolved therein. The chloride matrix ion species in the developing reagent and any in the sample diffuses across the boundary into the organic phase for exchange with the hydroxyl ions of the TOAOH which diffuse back into the aqueous phase. The chloride ion is retained by the TOAOH and flows out of the treatment zone in the organic phase. Thus, the organic phase contains TOACl while the aqueous phase contains $H_2O$ and NaOH. The system can be used to suppress other matrix ion species, typically acids (e.g., nitric acid or sulfuric acid). The analyte stream exits the chamber with the matrix ion species at a substantially lower concentration than when it enters the chamber.

The same principle can be used to suppress bases for the analysis of anions by appropriate change of the polarities. The organic liquid can be the same for either suppression of acids or bases.

The flow in all extant membrane-based suppression systems depart far from laminar conditions to limit axial dispersion and to promote transport to the membrane, which typically are the bounding walls. While this leads to efficient devices, the complex hydrodynamics makes it very difficult to model performance. Early models[27] could at best indicate limiting performance. Diffusional exchange in parallel co-current flowing streams is much more easily modeled. (It is also important to note here that the flow of two parallel streams in a microfluidic device will necessarily be co-current since attempts to establish countercurrent flow leads to a "short-circuit" between two adjacent inlet/outlets. This is different from the present practice of membrane-suppressors but similar to the flow schemes used in some special membrane-based applications.[28] However, co-current flow actually makes the task of numerical modeling easier.)

We assume that the total available channel length over which diffusional exchange is allowed to occur is L cm. Let the vertical depth of the channel be H cm. For simplicity, we assume that the eluent and exchanger phases occupy identical widths of W cm each. We also imagine that each flow stream is divided into p separate parallel streams of width $\Delta W$ cm each such that:

$$p = W/\Delta W \tag{1}$$

If F is the volumetric flow rate of each phase in $cm^3/s$, the average velocity is U cm/s where U is given by:

$$U = F/(WH) \tag{2}$$

Also, for simplicity, we assume that the two liquids have the same viscosity and are moving at the same flow rate, so that the pressure drops are the same. In our p parallel flow streams for each phase, if we designate stream 1 as the one at the wall and stream p to be the one at the interface and the center stream axial position $x_i$ of stream i (with maximum velocity occurring at $x_i = 0$) will be given by:

$$x_i = W - (i-1)\Delta W + \Delta W/2 \tag{3}$$

where i ranges from 1 to p. For laminar flow in a rectangular channel bounded by two parallel plates, the velocity is zero at the boundary layer and maximum at the center. The corresponding velocity in each of these streams is the average velocity U multiplied by the laminar flow profile factor $P_i$ where:

$$P_i = 1.5(1 - x_i/W)^2 \tag{4}$$

For computational simplicity, we have assumed that the velocity in each of these streams is actually the same but that the initial mass flux input is a function of the axial position.

If we assume that $\Delta L$ is the axial distance traveled during an infinitesimal computational time step $\Delta t$, it follow that:

$$\Delta L = U \Delta t \tag{5}$$

The system can thus be envisioned to contain p columns and q rows in each phase where:

$$q = L/\Delta L \tag{6}$$

The computation sequence is as follows: We designate the analyte concentration of the cell in the ith column and the kth row (row 1 is the input end and row q is the exit end) as $C_{i,k}$. For accounting of the mass flux, if the average input analyte concentration is $C_{IN}$ we populate the first row of cells ($C_{1,1}$ through $C_{p,1}$) in proportion to the velocity profile:

$$C_{i,1} = P_i C_{IN} \quad (7)$$

In the interfacial cell on the eluent side, where the eluent counterions diffuse to the interface, we assume that there is no resistance to interfacial exchange and all ions exported to the interface result in exchange as long as equilibrium or exchanger availability limitations do not set in (vide infra). The mean diffusion distance in the interfacial cell is $\Delta W/2$ with the eluent counterion concentration at the interface being zero. The concentration gradient for the diffusive transfer is computed on the basis of the actual concentration in the cell (not the amount used for mass flux accounting) such that the amount $\Delta m$ transferred from $C_{p,1}$ to the receptor interfacial cell is given by one-dimensional Fickian Diffusion to be:

$$\Delta m = DH\Delta L\Delta t \, C_{p,1}/(0.5\Delta W P_p) \quad (8)$$

where D is the diffusion coefficient of the eluent concentration. The transfer of this amount of the eluent counterior (say, chloride) to the corresponding interfacial cell in the exchanger phase (containing, for example, TOAOH) results in the release of OH⁻ to the aqueous phase interfacial cell. Relative to the transport of other ions, the transport of H+ and OH− are not rate limiting, and the exchange thus results in the formation of water. The exchange also results in the formation of TOACl and a concomitant decrease in the TOAOH concentrations in the interfacial cell in the exchanger phase. The concentration of TOACl in this cell, CClp,1 is then given by:

$$CCl_{p,1} = \Delta m/\Delta V \quad (9)$$

where $\Delta V$ is the volume of each cell.

$$\Delta V = H\Delta L\Delta W \quad (10)$$

The new concentration of the eluent counterion in the aqueous interfacial cell is:

$$C_{p,1} = (C_{p,1}\Delta V - \Delta m)/\Delta V \quad (11)$$

The TOACl concentration in the exchanger phase cells at the beginning of the experiment is set to zero while the TOAOH concentration $COH_{i,1}$ is set in the same way that the eluent concentration was set in eqn. 7 for mass flux accounting purposes:

$$COH_{i,1} = P_i COH_{IN} \quad (12)$$

Where $COH_{IN}$ is the entering TOAOH concentration. The diffusive step, with a diffusion distance of $\Delta W$ between adjacent cells then sequentially propagates from the interfacial boundary to the wall. In the exchanger phase, TOACl diffuses out to the wall and TOAOH diffuses toward the interface while in the eluent phase the eluent counterion diffuses to the interface:

$$\Delta Cl = D_{Cl} H\Delta L\Delta t (CCl_{p,1}/P_p - CCl_{p-1,1}/P_{p-1})/\Delta V \quad (13)$$

$$CCl_{p,1} = (CCl_{p,1}\Delta V - \Delta Cl)/\Delta V \quad (14)$$

$$CCl_{p-1,1} = (CCl_{p-1,1}\Delta V + \Delta Cl)/\Delta V \quad (15)$$

Where $\Delta Cl$ is the mass of TOACl transported between the specific pair of cells and $D_{Cl}$ is the diffusion coefficient of TOACl.

$$\Delta OH = D_{OH} H\Delta L\Delta t (COH_{p-1,1}/P_{p-1} - COH_{p-1}/P_p)/\Delta W \quad (16)$$

$$COH_{p-1} = (COH_{p-1}\Delta V + \Delta OH)/\Delta V \quad (17)$$

$$COH_{p-1,1} = (COH_{p-1,1}\Delta V - \Delta OH)/\Delta \quad (18)$$

Where $\Delta OH$ is the mass of TOAOH transported between the specific pair of cells and $D_{OH}$ is the diffusion coefficient of TOAOH.

$$\Delta E = DH\Delta L\Delta t(C_{p-1,1}/P_{p-1} - c/P_p)/\Delta W \quad (19)$$

$$C_{p,1} = (C_{p,1}\Delta V + \Delta E)/\Delta V \quad (20)$$

$$C_{p-1,1} = (C_{p-1,1}\Delta V - \Delta E)/\Delta V \quad (21)$$

Where $\Delta E$ is the mass of the eluent counterion transported between the specific pair of cells. Each triad of eqns. (13-15, 16-18, 19-21) are iterated from p=p to p=2 to complete the diffusive transfer in the first row of cells. At the end of this cycle, the contents of row 1 undergo translational movement to row 2 and the whole process is repeated until the end of q iterations where the contents now exit from the exchange process. At this point, the average concentration in the exit row is computed and compared with the input concentration to determine the fraction exchanged (extent of suppression).

Computationally, it is necessary to reduce the values of $\Delta W$ and $\Delta t$ until there is no further significant change in the results. In the computational results we present here, these values are 5 μm and 0.5 ms, respectively, to obtain virtually unchanging results in the range of other parameters used. There are two other caveats. After the completion of the computation of eqn. 18 in each cycle, one has available the concentration of all the relevant species that are involved in the transfer equilibrium (the concentration of chloride and hydroxide in the aqueous and the exchanger phases). While the equilibrium constant for TOAH in butanol and chloride in water is not known, we have used as a starting point the equilibrium constant (often referred to as the selectivity coefficient s) given for a strongly basic ion exchanger where:

$$S = (COH_{p,i} C_{p,i})/(CCl_{p,i}[OH^-_{p,i}]) \quad (22)$$

Since, for a strong eluent (and corresponding conclusions will be valid for a strong base eluent), we have (until the eluent is almost complete gone):

$$C_{p,i} = [H^+_{p,i}] \quad (23)$$

and:

$$[H^+_{p,i}][OH^-_{p,i}] = K_w \quad (24)$$

we can conclude that:

$$CCl_{p,i} = K_w COH_{p,i}(C_{p,i})^2/S \quad (25)$$

Eqn. 25 is one of the ultimate governing factors of the maximum amount that can be transferred. The second governing factor is the availability of the exchanger in the interfacial cell, which is replenished by diffusion. Especially in the case of suspension based exchange systems, this becomes the limiting factor. The computational algorithm takes the minimum allowed transfer, whether it is limited by eqn. 8, eqn. 25, or diffusional replenishment of the exchanger.

For a system with the eluent and exchanger phase each occupying a width of 500 μm, a length of 5 cm, with 10 mM HCl as eluent (Cl diffusion coefficient 2000 μm²/s) being exchanged with a hydroxide form anion exchanger, FIG. 1 shows the computed fraction exchanged as a function of flow rate for three different types of exchangers: (a) 1 μm size ion exchange resin suspension, (b) 100 nm size ion exchange resin suspension, and (c) dissolved TOAOH, the equivalent exchanger concentration being 50 mM in each case. The diffusion coefficient of the particulate exchangers were estimated, assuming spherical shape and the Stokes-Einstein equation, to be 0.215 and 2.15 µm²/s for 1 and 0.1 µm diameter particles, respectively. The diffusion coefficient of TOAOH was estimated from the equivalent conductance values of tetralkylammonium ions ranging from tetramethyl- to tetrabutyl- and applying a model:

$$G=(a+bn)^{-1} \quad (26)$$

Where G is the equivalent conductance of the tetraalkylammonium ion, n is the number of carbon atoms in the alkyl chain, and a and b are constants. The available data fits this model (linear correlation coefficient, $r^2$>0.99) and leads to an extrapolated value of G for TOA$^+$ of 11.1 S.cm² equivalent. The Nernst-Einstein equation then allows the estimation of the diffusion coefficient of TOAOH of TOACl (which are largely controlled by the size of the TOA$^+$ moiety) as 294 µm²/s. The results in FIG. 1 show that the dissolved exchanger with its much greater diffusion coefficient is obviously more effective. However, it would be possible to use a more concentrated suspension of a particulate exchanger without risk of bleedoff and confine it to a narrower section of the total channel width to make more efficient use of the exchanger.

In FIG. 2, we show other computational results for parametric variations. In FIG. 2A, the width of the 5 cm long channel is varied while 10 mM HCl is used as eluent and 50 mM TOAOH is used as the exchanger, both flowing at 5 µL/min. The greater efficiency of smaller channel widths is readily apparent.

Figure 2A:
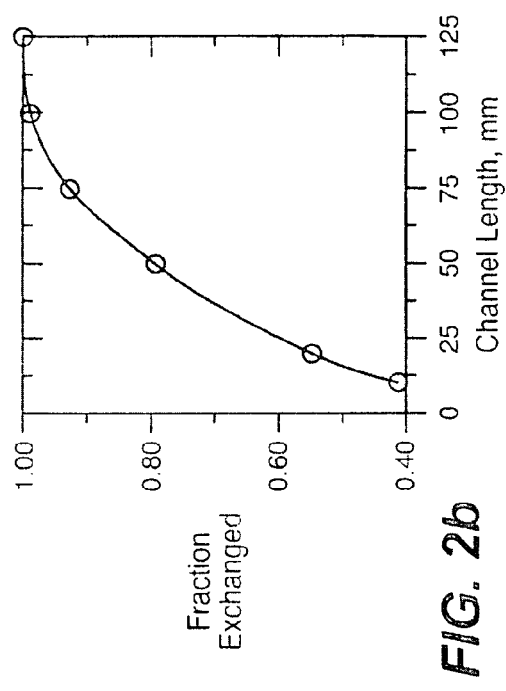
FIGS. 2A-2D. Model computations. The effect of variation of system parameters on the fraction of the eluent exchanged. See text for details.
Figure 2B:
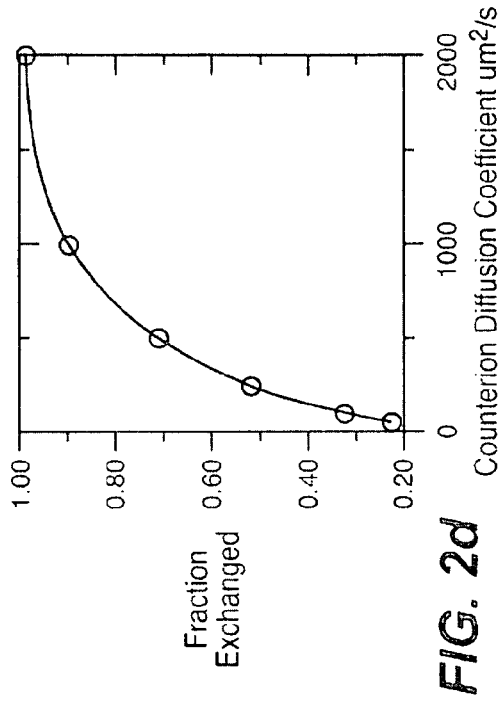
Figure 2C:
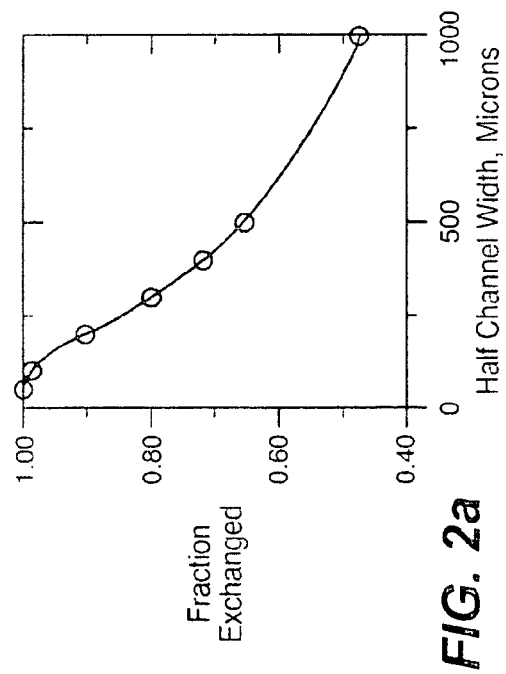
Figure 2D:
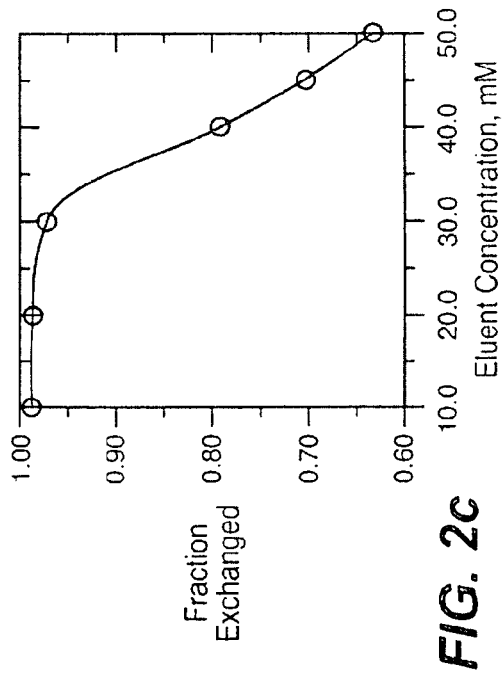

FIG. 2B shows a case where the fraction exchanged is plotted against the channel length for the suppression of 40 mM HCl with 50 mM TOAOH flowing at 5 µm/min in a device where each phase occupies a 100 µm width. Sufficient length is necessary to make good utilization of the regenerant even in a narrow channel width. FIG. 2C shows a case identical to that in FIG. 2B except that the channel length is fixed at 5 cm and the eluent concentration varied. This resembles typical suppressor behavior, insomuch as suppression is quantitative below some maximum eluent concentration. FIG. 2D has the other parameters set the same as FIGS. 2B and 2C except that the eluent concentration is fixed at 10 mM and the diffusion coefficient of the ion to be exchanged is varied. In cation chromatography, where either HCl or HClO$_4$ (or any other acid) can be used as eluent, it is advantageous to use a small mobile counterion containing acid such as HCl.

Suppression Using Colloidal Ion Exchanger Suspensions

Gjerde et al.[29] first described the use of ion exchange resin suspensions for conductivity suppression in IC. They demonstrated its use in the macro scale, deliberately mixing the resin suspension with the IC column effluent and passing the whole mixture through the detector and taking advantage of the fact that while suspended resin particles perform ion exchange, their large size makes minimal contribution to the conductivity of the mixed fluid. However, there is no particular advantage of this technique over membrane-based suppression in the macroscale and it has not been widely used. The applicability in the present case and its advantages are as follows. One does not really need to rely on the lack of contribution of these particles to the conductivity but to their low diffusivity (albeit the two parameters are inexorably tied by the Nernst-Einstein relationship). It is interesting to note that Yager et al.[9] have envisioned the detection of analyte molecules reacting with indicator-bearing particles to cause a detectable change in the particles. In the present case, detection occurs by removal of the eluent matrix by the particles; any conversion of the analyte counterion is only of secondary benefit. Thus, in a microfluidic device with two parallel streams, one containing small amounts of an analyte NaCl and larger amounts of an eluent NaOH and the other containing a cation exchange resin in H$^+$-form, the diffusive transfer and uptake of Na$^+$ and the counterdiffusion of the released H$^+$ will lead to the formation and successful detection of HCl in water.

The Complexing Form of Matrix Ion Species Capture Material

In this embodiment, the matrix ion species capture material is in liquid form dissolved in a lipophilic or organic carrier liquid phase. In this instance, the matrix ion species capture material does not remove the matrix ion species by an ion exchange reaction but instead by complexing with the matrix ion species counter ion molecule. In this instance, the matrix ion species capture material will be referred to as a matrix ion species complexing material. The mechanism can vary and may include salt formation, ion-pairing (ion-pair extraction), complexation, and other known mechanisms. The mechanism may also include a combination of ion exchange in complexing. Suitably, the organic carrier liquid may be of the same type as with respect to the ion exchange mechanism. Suitable matrix complexing materials include primary, secondary and tertiary amines for suppression of acid electrolytes. Suitable matrix molecule complexing materials for suppression of bases include well known complexing materials such as crowncarboxylic, cryptandcarboxylic acids or acyclic ether containing COOH functionality. The ability of such molecules to form complexes are well known. For instance, ion pairing mechanism can include that of tetraalkylammonium cation with inorganic anions such as chromate, perchlorate, thiocyanate or ion-pair extraction of anionic surfactants with methylene blue or any similar cationic compound. The ion-pair mechanism can also be used for extraction of cationic analyte ions with suitable anionic matrix ion-pairing materials.

By way of example, the organic phase carrier liquid can contain a secondary amine, such as one sold under the Amberlite-2. As above, the aqueous phase contains HCl electrolyte into which the analyte, sodium hydroxide is injected. During the process, the HCl is retained by the amine in molecular form. The exit of the treatment chamber, the organic phase contains the amine-HCl complex, while the aqueous phase contains a zone of NaCl. Some HCl will remain in the aqueous phase. That is acceptable within the common limits of ion chromatography suppression. The primary and tertiary amines should act in a similar manner. The underlying principle is believed to be that the amine reacts with an acid like HCl but not with a neutral salt like NaCl. With heavy metals, amine-loading metals such as Cu(II) for instance, complexes are formed with the amines and partially removed in the organic phase.

Following the extant wisdom, we initially believed that the "ion exchanger phase" must readily provide a source of H$^+$ or OH$^-$ ions to the aqueous phase for conductivity suppression of respectively a basic and an acidic eluent to occur. Indeed, the current practice of suppressed conductometric cation chromatography involves the use of strongly basic hydroxide from resin packed columns or membranes. While this is very useful for cations that are soluble in the free base (or hydroxide) form, such systems result in the precipitation of the hydroxides of non-alkali/alkaline earth metal cations, which thence cannot be detected by such means. It occurred to us that the use of an amine other than a quaternary amine in the present system would result in a situation where the amine will "soak up" the acidic eluent but may not take up the metal ion. In such a system, the conductivity of the eluent is largely removed but no anion exchange for hydroxide occurs. The disadvantage is that the analyte is not detected as the substantially more conductive hydroxide (for strongly basic analytes) form, but the advantage is that the analyte is never converted to hydroxide and will elute in conjunction with the eluent counterion form. This means that heavy metals that are normally inaccessible by suppressed conductometry can now be detected. A further advantage is that for weakly ionized bases, a linear response should be obtained without a "salt converter". This system is patentably useful for conductometric detection of heavy metals.

Suspension of Particles Removal Through Ion Exchange and Other Chemical Reactions In this mode, the matrix ion species capture material is a suspension of solid ion exchange, ion adsorption or ion complexation particles of suitable colloidal size. In this instance, the particles stay in the carrier liquid even if it is not an immiscible phase due to diffusion principles. Thus, the carrier phase may be an aqueous phase or an immiscible organic phase as described above. The ion exchange principles are similar to the above described ones for liquid ion exchange. Suitable ion exchange particles for suppression of acids include suspended particles, including base form anion exchange resin particles and particles capable of adsorbing or reacting with acid without release of highly conductive ionic species, e.g., hydroxyapatite, basic AlFe phosphate, etc. Also, removal of the matrix ion species may be facilitated by the use of ion exchange particles on which the matrix ion species precipitate. Thus, the ion exchange material. For example, the use of $Ag^+/Ba^{2+}$ ion immobilized on the ion exchange will precipitate $Cl^-$, $SO_4^{2-}$ and the like from the aqueous sample phase. The same principles apply for the ion exchange particles used for suppression of bases.

In yet another embodiment, a matrix ion species capture material is dissolved in the carrier liquid which reacts with the matrix ion-counter ion molecule diffusing across the interface between the two flowing liquids. In one embodiment of this for removal of an acid such as HI, the peroxide such as $H_2O_2$ is the matrix ion species capture material. The HI which diffuses across the interface reacts with the $H_2O_2$ to form $I_2$ and water, thereby suppressing the HI.

We have demonstrated continuous ion exchange in a shallow planar channel using parallel flow streams. Two approaches were used: (i) lipophilic ion exchanger dissolved in an immiscible organic phase, and (ii) aqueous suspension of finely ground ion exchange. Successful suppressed conductometric detection of 100 μM levels of analyte were attained. While this can be vastly improved on, this performance is much better than what has thus far been attained in planar microdevices. Ion exchange with a solution of secondary amine (Amberlite LA-2) was found to make the suppressed conductometric detection of heavy metals possible since removal of the eluent acid by the amine, rather than anion exchange, occurs. When colloidal ion exchange resin suspensions are used, no organic solvents are needed.

The present technique provides a means for an efficient microscale suppression in microscale devices without a membrane. Conductometric detection is such devices is simpler than almost any other detection mode when external apparati must be kept to a minimum. There is a clear advantage in lowering channel width further and the present work suggests that smaller, truly microfabricated devices will product much better results. The system can obviously be applied for other post-column reactions.

Vertically Stratified Flow

Side by side (horizontal) flows in microfluidic channels provide efficient means for various chemical reactions occurring by diffusion. The diffusion path is determined by the total width of the channel and the widths of the concurrent flows inside the channel. It appears that vertically stratified horizontal flows offer an interesting alternative to these approaches. We demonstrate a microfluidic system, in which two immiscible liquids flow horizontally, one on top of another, in a shallow channel and continuous extraction or ion exchange takes place. The diffusion path for the reaction to occur is given by the thickness of the respective horizontal liquid streams in the channel.

In this embodiment, two immiscible liquids (the same stream and carrier stream) are vertically stratified in horizontal flow in microfluidic channels. The horizontal flow design is an alternative to the side-by-side approach described above, since the path for the diffusional chemical reactions in the system is defined by the thickness of the respective layered flows, while the width of the channel is not important. Shorter diffusion paths are achievable, the system can be used at higher flow rates than normally required with the side-by-side design because with larger channel widths, a greater exchange area is achieved and the same flow velocity results in an increased flow rate and such a system can also be used for running parallel assays. In one embodiment, the layer formation was simulated and some physical properties of the liquids to form horizontally layered flows were experimentally confirmed. Practical applications of the system include ion-pair extraction of anionic surfactant (dodecylbenzenesulfonic acid) with MB into hexanol, ion exchange of chromate anion into the butanolic phase containing tetraoctylammonium bromide (TOABr) and continuous ion exchange/conductivity suppression with secondary type amine Amberlite LA-2.

Operation of the device, Principles. The successful formation of vertically stratified horizontical flows of two immiscible liquids is governed by the physical properties of the two liquids, such as density, viscosity and interfacial tension between the two liquids in contact. The interfacial tension and density, as originally thought, should have an effect on the layer formation and these parameters were studied in the initial experiments. When two immiscible phases are brought into contact, their boundary has a contractile tendency, corresponding to the interfacial tension, $\gamma_i$. The values of interfacial tension of various organic liquids and water (aqueous solution) and other physical properties are summarized in the Table 2:

TABLE 2

Physical properties of various organic liquids.

| | $\gamma_i$ | $\gamma_o$ | $\rho$ | $\eta$ |
|---|---|---|---|---|
| Butanol | 1.8 | 24.6 | 0.81 | 2.30 |
| Pentanol | 4.4 | 25.4 | 0.81 | 4.70 |
| Hexanol | 6.8 | 25.8 | 0.81 | 5.10 |
| Benzylalcohol | 4.8 | 39.7 | 1.04 | 5.80 |
| Chloroform | 32.8 | 27.1 | 1.49 | 0.58 |
| Hexane | 51.1 | 18.4 | 0.66 | 0.33 |

$\gamma_i$ interfacial tension of respective solvent and water ($\times 10^{-3}$ N.m$^{-1}$)
$\gamma_o$ surface tension against air ($\times 10^{-3}$ N.m$^{-1}$)
$\rho$ density (g.cm$^{-3}$); $\eta$ viscosity (centipoise)

It can be seen that the interfacial tension between water and short alkyl chain alcohols and benzylalcohol is significantly lower than that between water and other organic solvents, owing to the presence of the polar hydroxyl groups. The molecules with polar groups concentrate at the boundary of the two phases and the hydroxyl groups orientate towards the aqueous phase, resulting in a low standard free energy at the interface and hence a low value of interfacial tension[22].

When performing the experiments with set of solvents, the horizontal flows could be established for all alcohols, but not for chloroform nor hexane. An axially segmented flow that arises from the break-up of the layered inlet flow immediately upon entering the channel was observed for these solvents. This is in agreement with the $\gamma_i$ values shown in the Table 1. Addition of more than 30% of butanol into these organic solvents proved to decrease the interfacial tension to such an extent that the two horizontal layers could be formed.

Contrary to intuitive expectations, the density of the immiscible liquids did not appear to have any effect on the stability of the flows. In an experiment, when stable horizontally layered flow of aqueous solution of methylene blue and butanol were formed, turning the device upside down so that the liquid of the higher density (aqueous solution of MB) now appeared in the lower layer did not disrupt the stable stratified flow. This phenomenon was later confirmed using the flow simulations.

It is interesting to note that the observed flow interface tends to decrease its surface area to minimize the free energy at the boundary and consequently its shape is not flat but curved.

Simulation of the Flows in the Vertical Microfluidic Device.

In the experiments described above, we have confirmed a stable layered flow corresponding to the layered inlet geometry. We have also observed an axially segmented flow that arises from the break-up of the layered inlet flow immediately upon entering the channel. The purpose of the modeling effort described in this Section is to identify the factors that determine which configuration a particular flow will assume. We also seek a quantitative tool to design parameter values that will ensure a stable layered flow.

We model the flow using a computational fluid dynamics (CFD) package called CFD-ACE [CFDRC]. This package includes a wide variety of physics models, including interface tracking and surface tension effects. Using CFD-ACE we activate and deactivate various physical effects and adjust property values, and observe the effect on the flow. This type of study is uniquely enabled by CFD software, since designing experiments to remove the effects of gravity or surface tension, for example, is likely to be extremely difficult.

The geometry modeled is a straight channel flow, 45 mm long by 2 mm wide by 400 µm deep. Two liquids enter the channel at z=0 with specified velocity, one occupying the upper half of the inlet (0<y<200 µm) the other occupying the lower half (−200 µm<y<0). The fluid exits at the z=45 mm plane, at a specified pressure relative to ambient of 0. To reduce computation time, a symmetry boundary condition is enforced at x=0, and only the half of the channel from x=0 to x=1 mm is actually simulated. Two flows are simulated. The first has butanol entering in the top slot and water in the bottom. The second has water in the top slot, and chloroform in the bottom. Table 3 lists the properties used in this simulation.

TABLE 3

Properties of solutions for simulation of horizontally layered flows.

| | $\gamma_i$ | α | ρ | η |
|---|---|---|---|---|
| Water | — | — | 1.00 | 8.55 |
| Butanol | 1.8[a] | 83 | 0.80 | 6.88 |
| Chloroform | 32.8[b] | 106 | 1.48 | 5.40 |

$\gamma_i$ interfacial tension ($\times 10^{-3}$ N.m$^{-1}$)
α wetting angle (deg)
ρ density (g.cm$^{-3}$)
η dynamic viscosity $\times 10^{-4}$ (kg.m$^{-1}$.s$^{-1}$)
[a]interfacial tension butanol/water
[b]interfacial tension chloroform/water The volume-of-fluid (VOF) interface model was used to track the fluid interface. Full surface tension effects were activated, including both normal and tangential surface tension forces. Gravity was applied in the negative z-direction. FIG. 9 shows the results at various input velocities. As can be seen there, the layered configuration becomes stable for the butanol/water flow at somewhere between 5 and 10 mm/sec input velocities, while the chloroform/water flow always assumes the segmented configuration. Experimentally the butanol/water layered flow became stable between 1 and 5 mm/sec, while the chloroform/water layered flow could not be stabilized at any velocity. Thus we have a good qualitative prediction of the flow behavior, but the simulation accuracy does not seem sufficient for high precision modeling.

Figure 10A:
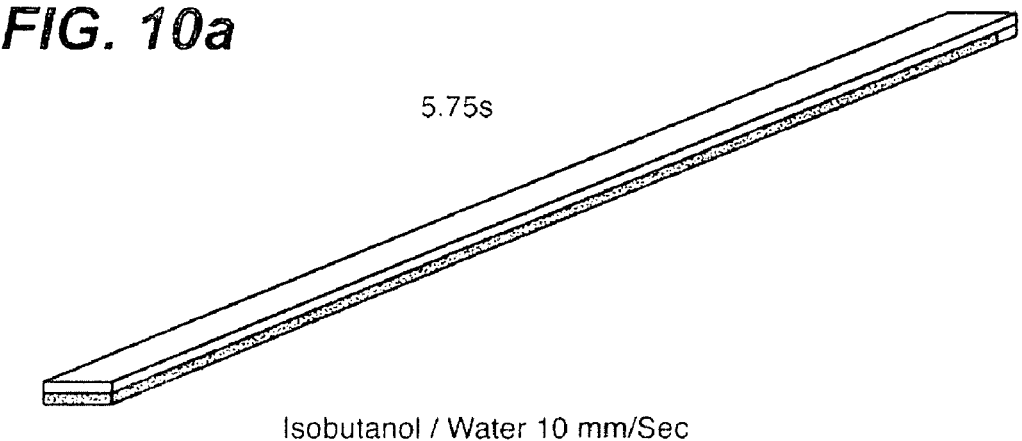
FIGS. 10A-10C. Simulation of the effect of selected physical properties of the liquids on the formation of horizontally layered flows in the butanol/water system. (a)—reversed gravity, (b)—the effect of various contact angles, (c)—increase in the interfacial surface tension.
Figure 10B:
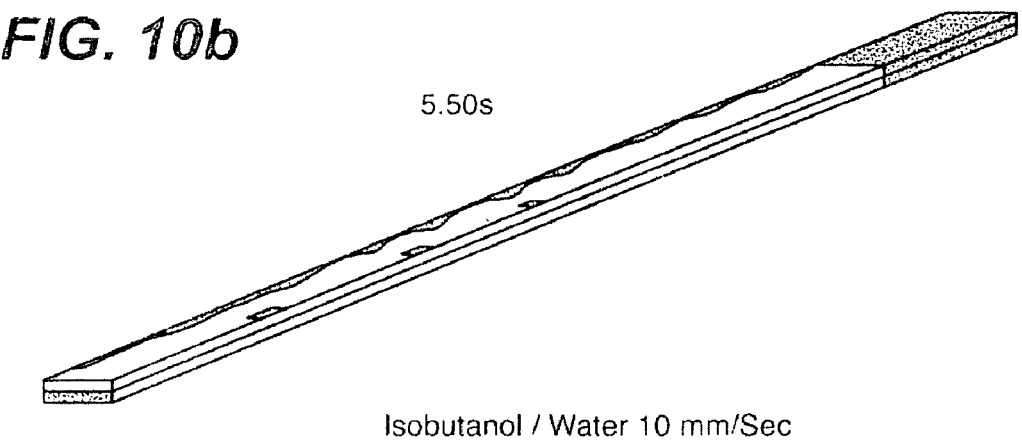

Parameters relating to the stability of the flow pattern include density, interfacial surface tension and wetting angle. Investigations were performed using a 1 cm channel. Butanol is less dense than water, hence the layered configuration studied in which butanol flows on top should be stabilized by buoyancy effects. However flow experiments indicate that the butanol/water layered flow is also stable when butanol enters on the bottom. To test this in simulation the direction of gravity was reversed. As can be seen from FIG. 10A this layered flow is stable. The "wettability" of the channel walls is characterized by the interior contact angle of a drop of liquid on the channel surface surrounded by water. A contact angle of 0 degrees indicates perfect wetting, while a contact angle of 180 degrees indicates that the liquid does not wet. Because the sidewalls of our channels are made of several different materials, namely electrical tape and transparency film, while the floor and ceiling are glass, several values were considered. These were 0, 30, 60, 90, 120, 150 and 180. Selected results are shown in FIG. 10B.

Figure 10C:
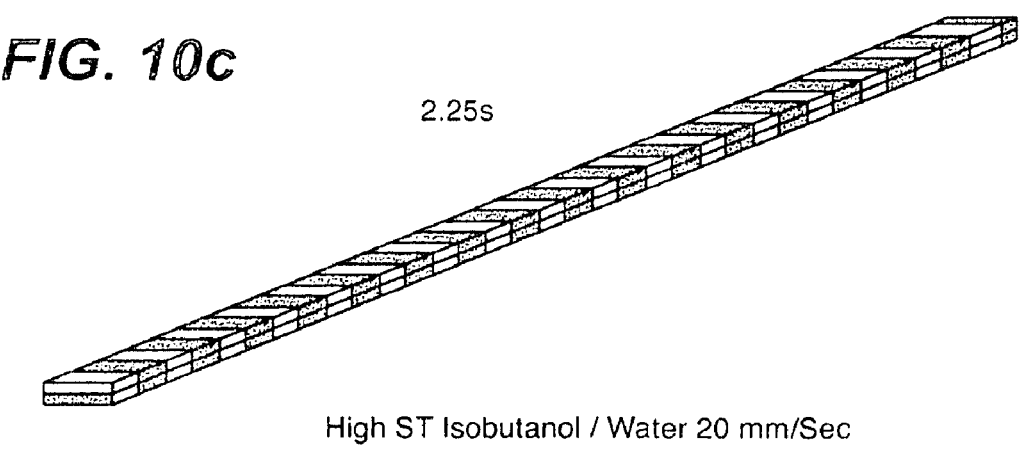

To test the effect of surface tension we re-ran the 20 mm/sec butanol/water case, but with the value for interfacial surface tension changed from that of butanol to that of chloroform. The resulting flow segments, as is shown in FIG. 10C. Recall that the 20 mm/sec isobutanol/water layered flow is stable. Therefore the interfacial surface tension seems to be a major factor determining a stable flow configuration.

Figure 11A:
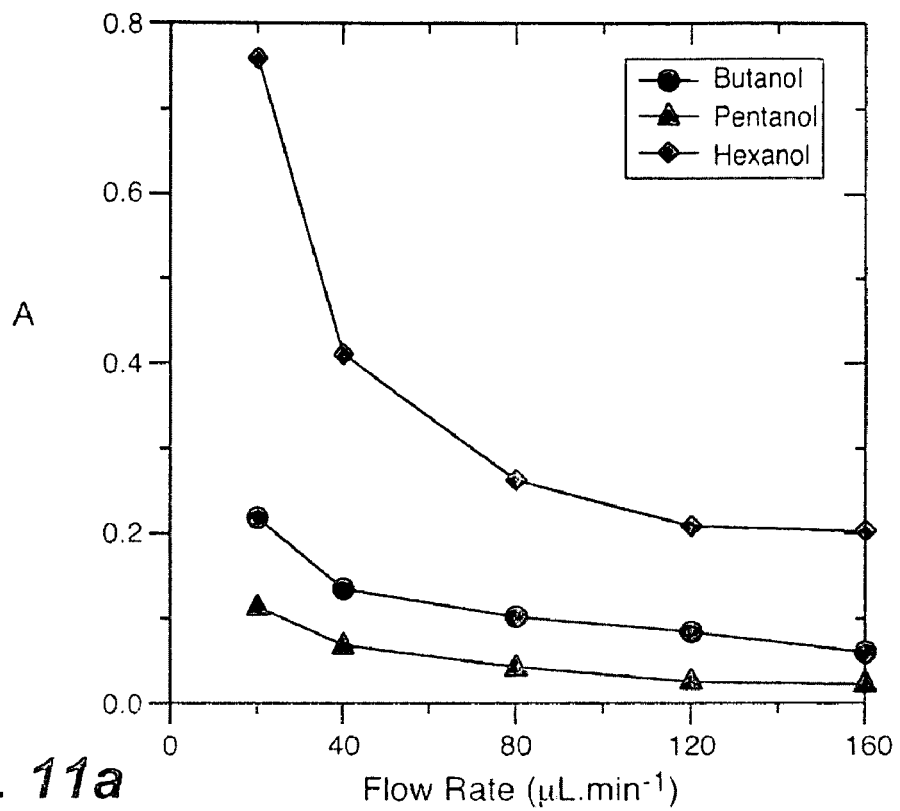
FIG. 11. The effect of the flow rate (a) and channel depth (b) on the extraction efficiency of 1 mM methylene blue (MB). Conditions: (a) channel depth: 400 μm, (b) flow rate: 40 μl.min$^{-1}$, absorbance of the collected and diluted solutions measured at 565 nm.

Continuous extraction. To study the function and parameters of the microfluidic device with the horizontal flows a model extraction system was designed. A 1 mM solution of methylene blue (MB) in deionized water was aspirated through the device on the bottom of the channel and an immiscible solution of a short chain aliphatic alcohol on the top of the channel. The upper organic phase with the extracted MB was collected, diluted with respective solvent and its absorbance was measured at 656 nm. The results of varying the flow rates between 20 and 160 µL/min is shown in FIG. 11A. The efficiency of the extraction increases with decreasing the flow rate, as expected from the Fick's law of diffusion.

A significant difference between the amount of MB extracted into different alcohols can be observed too. The low extraction efficiency of hexanol could be advantageously used for ion-pair extraction of MB and anionic surfactant (DBSA).

Figure 11B:
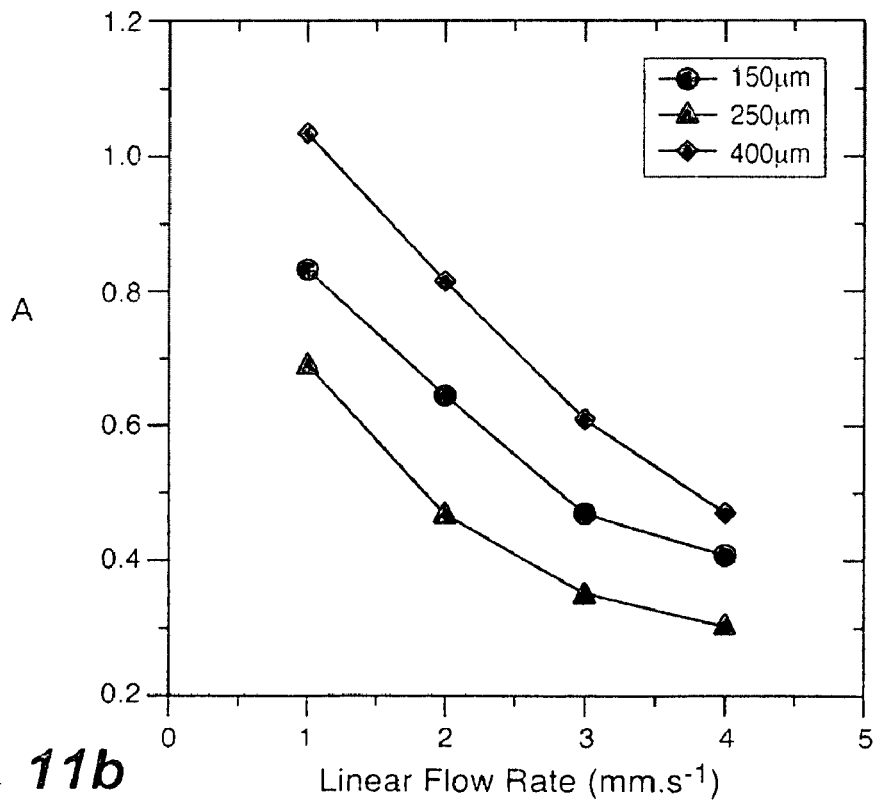

On FIG. 11, the effect of the channel depth on the extraction is shown. The same solutions as in FIG. 11A were used in three channels differing only in the depth. The volumetric flow rates were recalculated to the linear flow rates in mm/s to achieve the same contact time of the solutions in respective channels. In the design with the channel depth of 150 μm, the thickness of the layered flows is approximately 75 μm, e.g. the diffusion path for the methylene blue is almost 3 times shorter than for the depth of 400 μm Clearly the decrease in channel depth favors the extraction.

In a channel of the same dimensions, the diffusion path in the side by side configuration, would be as high as 1 mm. To demonstrate the effect of the diffusion path length on the extraction in a horizontal- and side by side flow designs a channel 400 μm deep, 45 mm long and 2 mm wide was used in both cases. The linear flow rates were the same, since the volume of the channels was identical. In the first case, the liquids were allowed to flow horizontally, e.g. the diffusion path was ca. 200 μm. In the second case, the liquid flow was parallel, e.g. the diffusion path was ca 1000 μm. The organic phase with the extracted MB was collected, diluted and its absorbance was measured at 656 nm. The flow rates were varied between 20 and 160 uL/min and the for each selected flow rate the ratio of measured absorbance was calculated. The signal enhancement (expressed as the ratio of measured absorbance values after dilution) ranged from 17 to 100 for the flow rates 20 and 160 μL/min respectively. This clearly demonstrates the advantage of the horizontally layered flow design.

Ion-Pair Extraction. Determination of Anionic Surfactants.

Figure 12A:
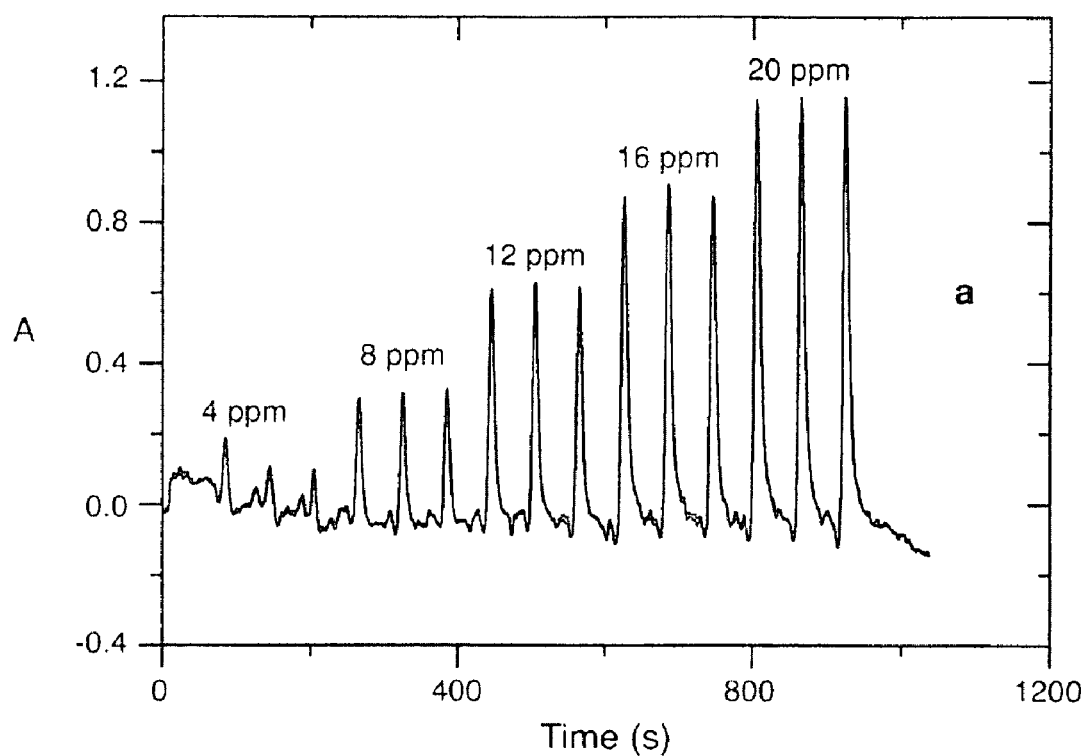
FIG. 12. Extraction of DBSA-MB ion pair into hexanol. (a)—calibration graph for 2-20 ppm DBSA, (b, c)—12 repeated injections of 12 ppm and 6 ppm DBSA standard. Conditions: channel depth 400 μm, flow rate 40 μl.min$^{-1}$, injection volume 5 μL, absorbance measured at 565 nm.
Figure 12B:
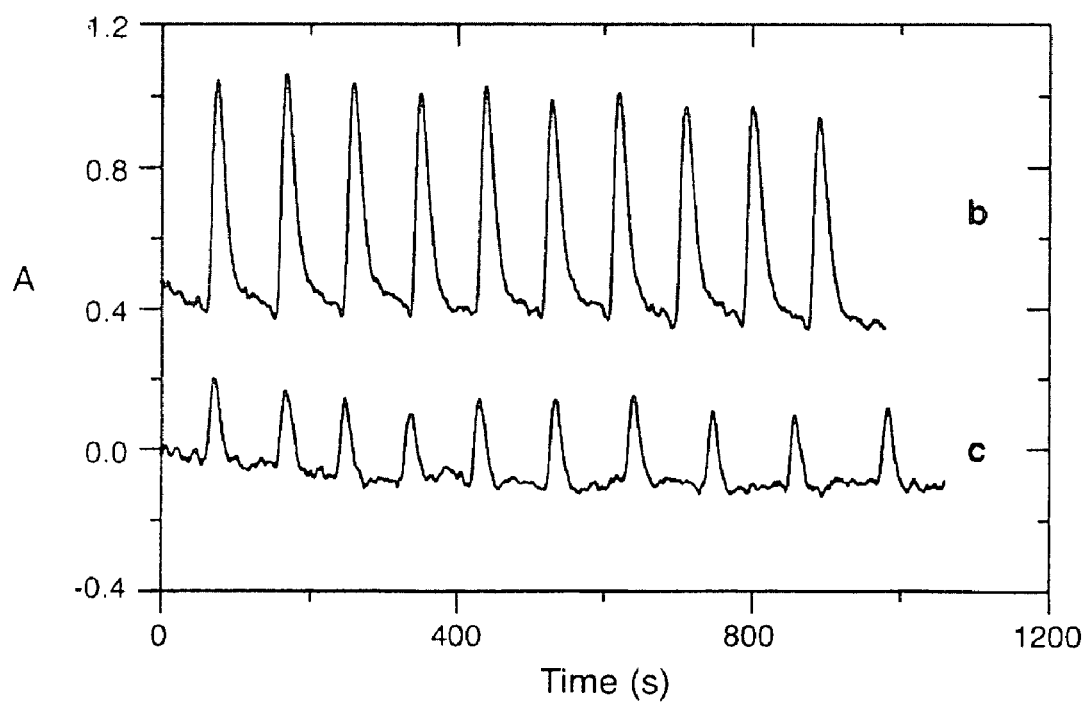
Figure 13:
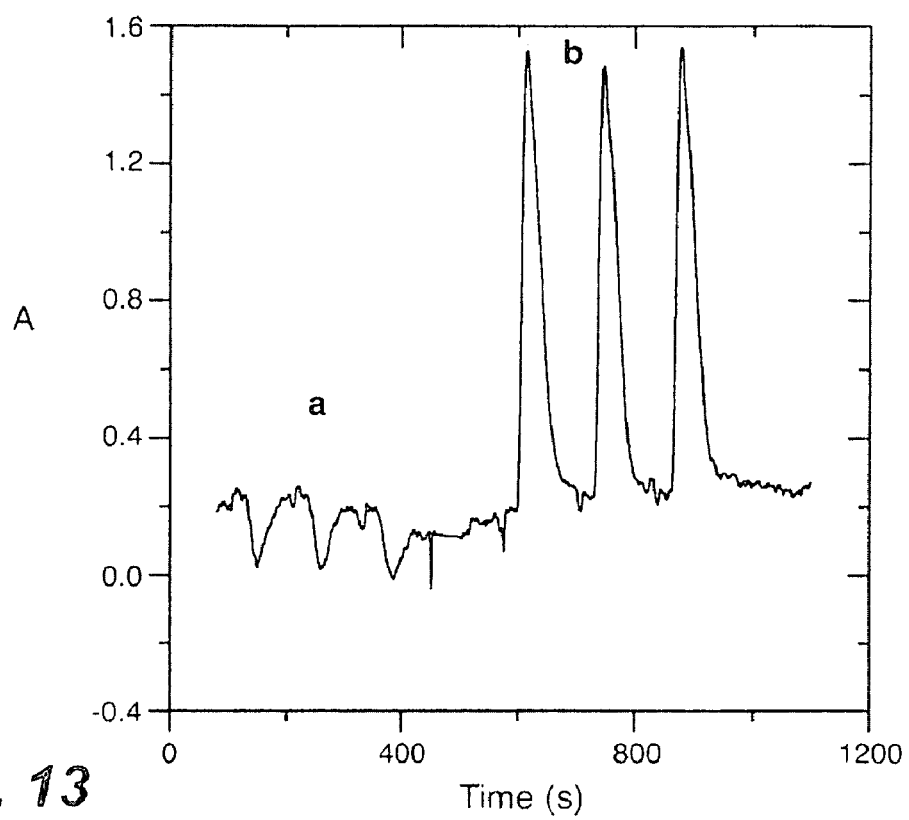
FIG. 13. Analysis of extractable matter in tap water. (a) 3 injections of deionized water, (b) 3 injections of tap water. Conditions the same as in FIG. 5.

The extraction efficiency of methylene blue into hexanol is rather poor as shown in FIG. 11A. The amount of MB extracted can however be significantly enhanced by addition of ion-pairing agent such as anionic surfactant. On contrary, the co-extraction of the ion pair MB-anionic surfactant can be used for the determination of concentration of anionic surfactants in the samples. The difference in extraction of MB and MB-anionic surfactant ion pair was examined on the model system with DBSA. A 0.2 mM solution of methylene blue (MB) in deionized water was aspirated through the bottom of the channel 1 and hexanol was aspirated through the top. The DBSA solution in the range 0-20 ppm was injected into the aqueous phase and the extracted ion pair of DBSA-MB was measured using a capillary cell UV detector. The calibration for DBSA is depicted on FIG. 12a. The calibration was linear in the range 0-20 ppm ($r^2$=0.998). On FIGS. 12b and 12c, the repeatability of 10 injections of 6 and 12 ppm of DBSA, respectively, is shown. The r.s.d. values ranged from 3.3% and 8.6%. On FIG. 13, 3 injections of a blank, e.g. deionized water and 3 injections of tap water into MB-stream were performed. The blank trace shows small negative peaks, resulting from dilution of MB carrier stream. The peaks for tap water correspond to MB-extractable matter.

It is important to mention that the ratio of the horizontal flows through the channel significantly influences the system performance and extraction efficiency and consequently also the peak shapes. 20 ppm of DBSA was injected into the aqueous MB stream aspirated through the device. The ratio and hence the thickness of the two horizontal was adjusted by the height of the reservoirs. The volumetric flow ratio of the two phases could be manipulated from 1:1 to 3:1, which corresponds to the flow rates of 60 to 90 μL/min for the hexanolic phase and the flow rates of 60 to 30 μL/min for the aqueous phase. At the phase ratios 1:1 the peaks were much higher than at phase ratios 3:1, e.g. maximum extraction efficiency and best peak shapes were achieved at minimum flow rates of the organic phase. Keeping the total volumetric flow rate through the device constant this in turn means that the thickness of the vertical layers is changed, minimal thickness of the organic phase is obtained at its lowest flow rate.

Figure 14:
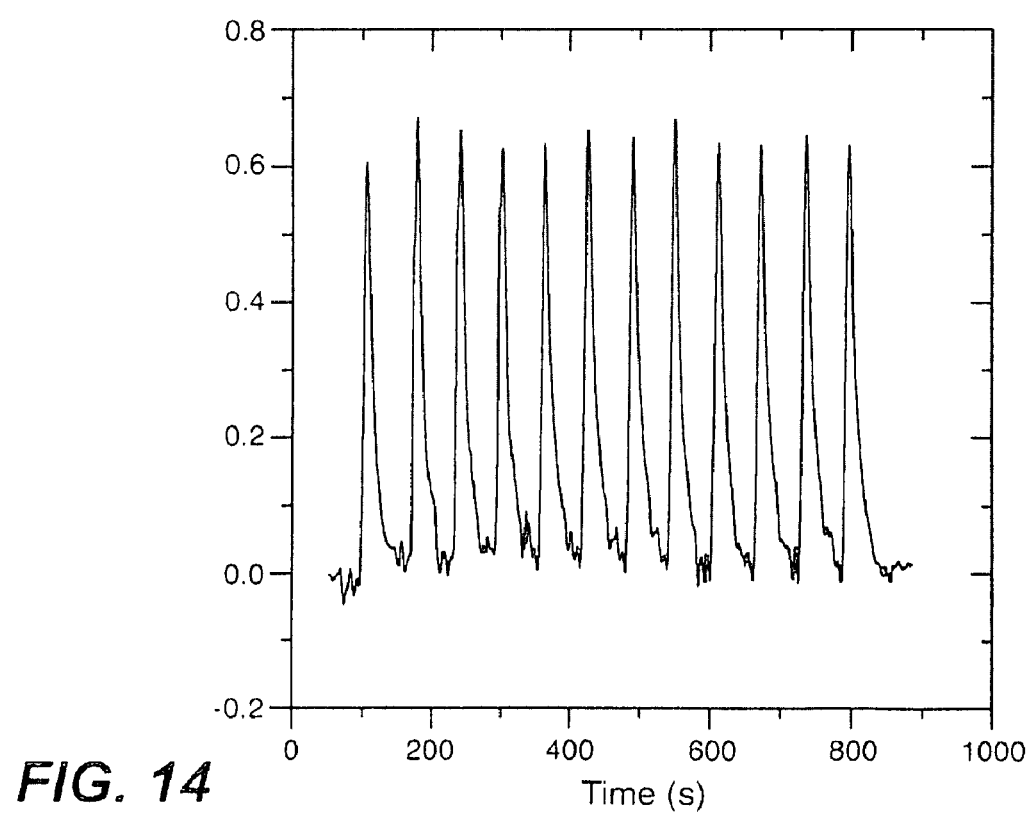
FIG. 14. 12 repeated injections of 1 mM potassium chromate. Conditions: channel depth 400 μm, flow rate 40 μl.min$^-$ $_1$, injection volume 5 μL, absorbance measured at 372 mm.

Ion-pair extraction of chromate into butanol. The ion-pair assisted extraction in the system with horizontal flows can be further exploited by extracting an anionic molecule from the aqueous phase with the ion-pairing reagent incorporated in the organic phase. The chromate anion is not extracted into butanol, however addition of 2% TOABr into the butanolic phase allowed the transfer of $CrO_4^{2-}$ into the organic phase with Br being released into the aqueous phase. A 10 mM NaOH was used as a carrier solution and aqueous solution of potassium chromate was injected into this stream. The repeatability of 12 injections of 1 mM $K_2CrO_4$ extracted into the 2% butanolic solution of TOABr is shown on FIG. 14, with r.s.d. of 2.6%.

Figure 15A:
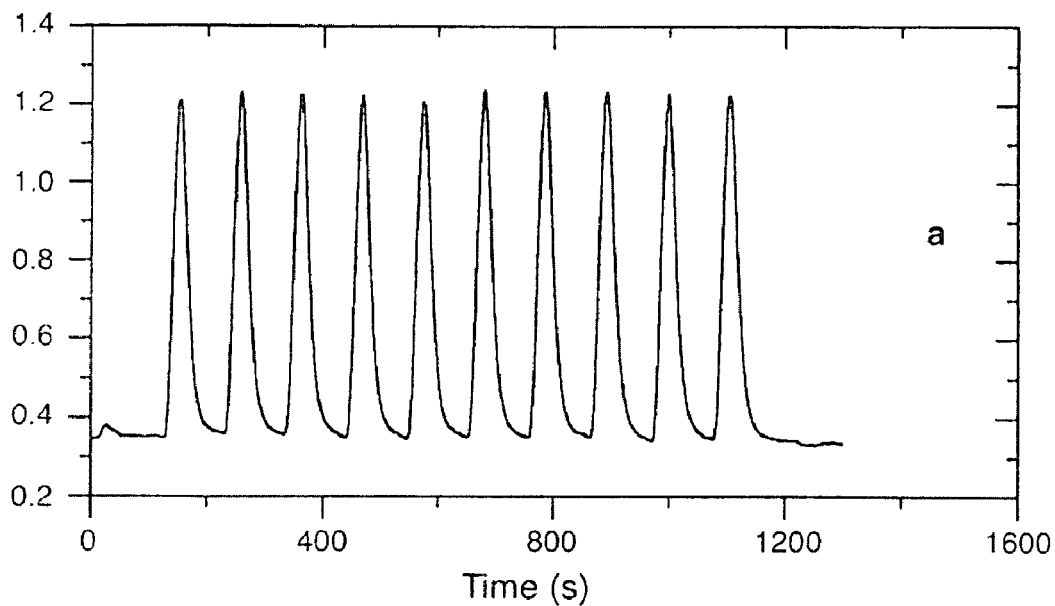
FIGS. 15A-15B. Ion exchange/suppression in two immiscible liquids. (a) 12 injections of 1 mM NaCl into 1 mM HCl. Ion exchanger: 1% Amberlite LA-2 in butanol. Conditions: channel depth 400 μm, flow rate 20 μl.min$^{-1}$, injection volume 5 μL, conductivity detection.
Figure 15B:
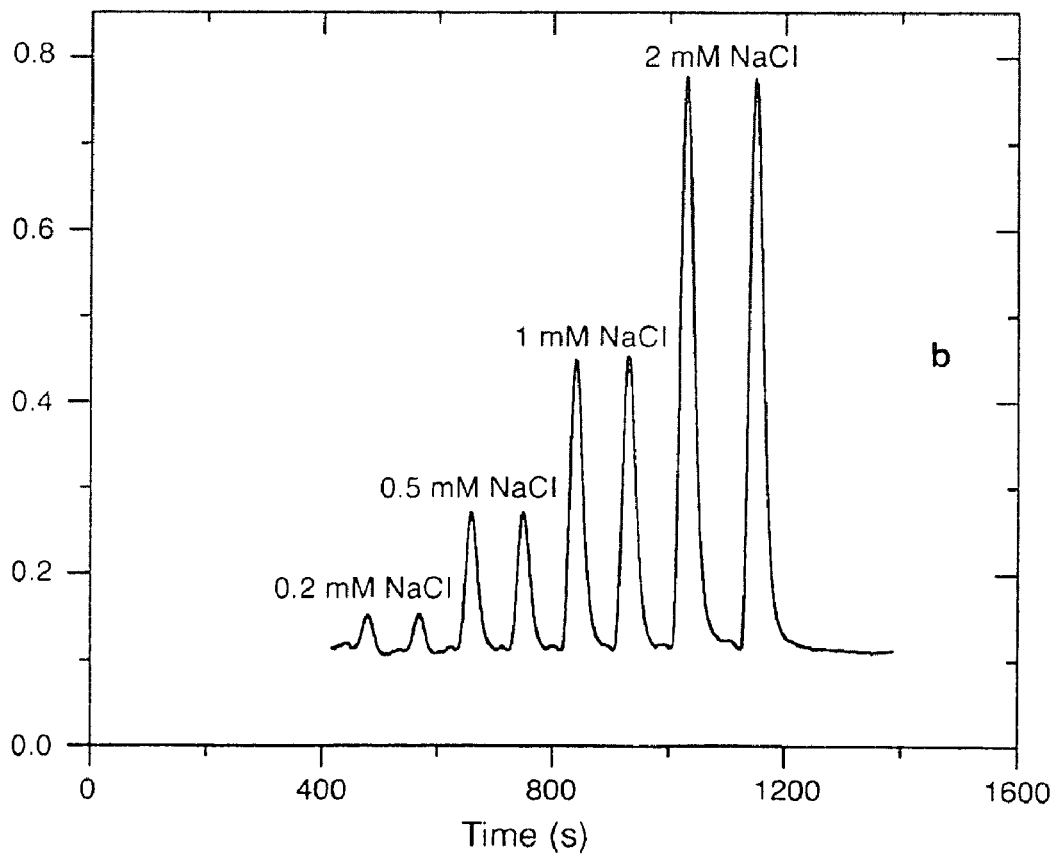

Conductivity suppression. In the first section, we have demonstrated continuous ion exchange in side-by-side flows in a shallow planar channel. A lipophilic ion exchanger was dissolved in an immiscible organic phase flowing parallel side-by side with the eluent stream of strong mineral acid (1-10 mM HCl). A strongly basic compound, such as tetraoctylammonium hydroxide (TOAOH), or a secondary amine, e.g., Amberlite LA-2, were used and proved to be equally efficient for suppression of the conductivity of the eluent phase. Amberlite LA-2 was used exclusively in this study, since it does not significantly change the interfacial surface tension of butanol/water, as does the addition of TOAOH. FIG. 15A shows 12 injections of 1 mM NaCl into a 1 mM HCl eluent, using 1% Amberlite LA-2 in butanol as the ion exchanger. The flow rates of the eluent and ion exchanger were 20 μL min$^{-1}$. The calibration was linear in the range 0-2 mM NaCl (see FIG. 15B) and the estimated S/N=3 limit of detection (LOD) from these data is ≦0.1 mM NaCl, largely controlled by dispersion in the injector and the suppression device as well as the larger than optimum detection electrodes; the detector electronics used here is also dated.

We have shown practical application of vertically stratified horizontal flow in microfluidic channels. The configuration of horizontal is beneficial compared to the side-design, due to the decreased diffusion path allowing higher flow rates to be used at the same performance. The applicability of the system was demonstrated on continuous extraction of methylene blue into different organic solvents, ion-pair extraction and ion exchange. The system can possibly used for running parallel assays, since the width of the microfluidic channel is not limited.

The footnoted references are listed in the Literature Cited.

In order to illustrate the present invention, the following examples of its practice are provided.

EXAMPLE 1

Figure 16A:
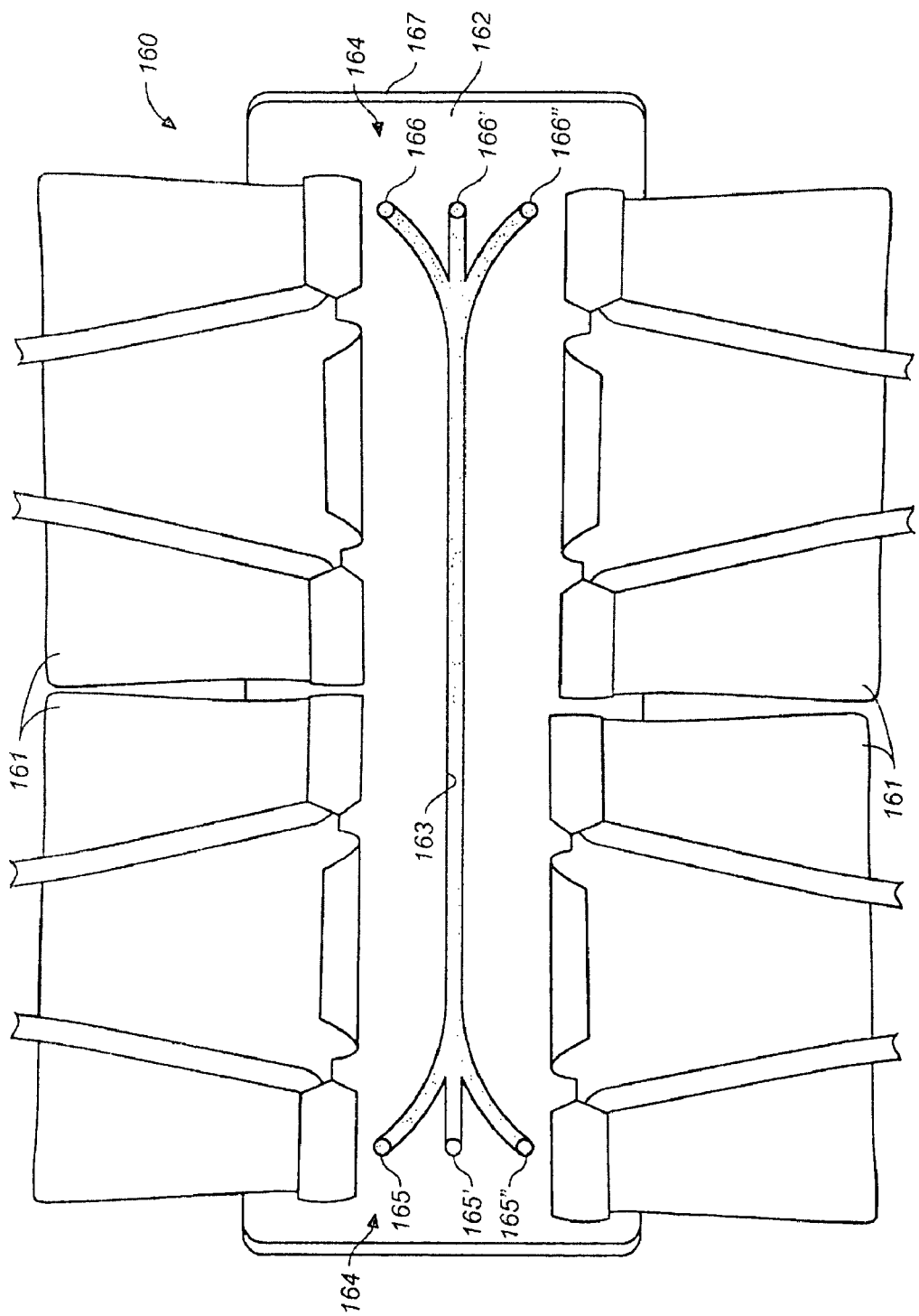

Device. Whitesides and Stroock[25] have recently described versatile flexible methods to construct microfluidic devices, especially by soft lithography. We have recently described a "strings and sealing wax" approach to experimenting with flow in shallow planar devices 160 using tapes/thin sheets as spacers and with binder clips 161 to hold things together. The present device constituted of a 6 mm thick 25×75 mm fluorinated ethylene-propylene copolymer (FEP) sheet 162. A channel 163 (50×1×0.1 mm L×W×D, computed volume 5

μL) with a trifurcation at each end 164 (constituting 3 inlets 165, 165', 165" and 3 outlets 166, 166', 166" with 0.5 mm apertures drilled through the FEP sheet) was inscribed on the FEP surface by conventional machining. The channel 163 was sealed at the top by a microscope slide 167, held together by binder clips 161. The device is shown in FIG. 16A.

Although the device 160 can be used with three parallel flow streams (an "eluent" stream 168 to be suppressed, an immiscible stream functioning as a liquid membrane 169, and a regenerant stream to regenerate the "membrane"), experience showed that the consumption of liquid is small and in-situ "regeneration" is not especially worthwhile (regeneration, if desired, is better conducted off-line). All experiments reported here are based on two liquid streams. In some cases the central inlet/outlet port 165'/166' were not used at all, in others, two sets of adjacent inlet/outlet ports 165' & 165"/166' & 166", including the central one 165', 166', were used with a solution/suspension of the exchanger phase 170 to limit the width of the eluent phase 168.

Initial experiments also showed that the hydraulic resistance of the device is relatively small. Even a 10 cm hydrostatic head produced flow rates much higher than that desired. The respective liquids were therefore aspirated by a peristaltic pump (Miniplus 2, Gilson) from the device outlets at 2-10 μL/min. The liquids were aspirated at given flow rates from all three outlets, thus the total volumetric flow rate was the sum of the individual flow rates from the three outlets. The inlet liquid reservoirs were connected to the device with large bore tubing (1.25 mm) to eliminate any flow resistance. Normally the inlet reservoirs were maintained at a hydrostatic height of 10 cm. However, the reservoir heights were adjusted to modify the widths of the individual streams 168, 170 flowing through the channel 163, from only one liquid, to width ratios of 1:3 to 3:1 (see FIG. 16B, 16D, respectively). The change in width effectively changes the residence time. For quantitative exchange experiments, it also changes the mean diffusion distance for the exchangeable ion in the "eluent" stream 168 to the exchange interface 169.

The conductivity detection electrodes were constituted of a concentric cell consisting of an inner stainless steel tube (175 μm id, 350 μm od) and an outer stainless tube (575 μm id, 1.05 mm od) separated by a PTFE tube acting as a spacer. This assembly was placed in the exit of the channel used for the eluent phase. The electrodes are large relative to channel dimensions and contribute to band-broadening. The electrodes were connected to a relatively early model commercial conductivity detector (Model CDM-1, Dionex Corp.). No preamplifier[4] was used and S/N was not optimized. Injections into the eluent stream were made with a loop-type valve timed to inject ~650 nL.

Reagents. All chemicals used were of reagent grade. Tetraoctylammonium bromide (TOABr, Sigma-Aldrich), dodecylbenzenesulfonic acid (DBSA, Stephan Chemical, Northfield, Ill.), sodium hexadecylsulfonate (Na-HDSA, Sigma-Aldrich, 98%), sodium octadecylsulfonate (Na-ODSA, TCI America) were obtained as listed. Stock solutions (each 100 mM) of NaOH, HCl and NaCl and various heavy metal salts (in chloride, sulfate and nitrate form) were diluted to the desired concentrations with deionized (DI) water. Amberlite LA-2 (Aldrich), a secondary amine type anion exchanger, was used without further purification. Butanol (EM Science) was used for the preparation of water-immiscible solutions of liquid ion exchangers. Typically, solutions were degassed by ultrasonication prior to use but reagents were not pretreated beyond this.

Preparation of liquid anion exchanger. A 150 mM butanolic solution of TOABr was converted to the hydroxide form by passing through a strongly basic anion exchange resin column (Dowex 1×8-100) in $OH^-$-form. (The resin column was pretreated with 5 bed volume of 1 M NaOH, followed by extensive rinsing with deionized water, followed by ethanol as an intermediate solvent and finally washing with butanol.) The first portion of the TOAOH eluent was discarded. Triton X-100 (BioRad) was added to the collected TOAOH fraction to have a concentration of 1%. Triton-X was not pre-cleaned to remove ionic impurities.

Preparation of liquid cation exchanger. DBSA was dissolved in butanol to have a 100 mM concentration. To obtain HDSA and ODSA in butanol, a 100 mM suspension of the respective salt was mixed with a strong acid form cation exchange resin in $H^+$-form (Dowex 50Wx8-100, twice the stoichiometric amount necessary for exchange taken). The suspension was sonicated for 10 min until complete dissolution was observed. The supernatant was then taken. Sulfate/sulfuric acid are always present in these solutions. An attempt was made to remove at least some of the sulfate present by treating the solution with an aliquot of $Ba^{2+}$-form Dowex 50Wx8-100 resin, taken in an amount corresponding to 5% of the total mount of the acid taken. After 10 min of sonication, the solution was filtered through a glass-fiber filter. Triton X-100 was added to the final solution to a concentration of 2%.

Preparation of ion exchange resin suspension. Dowex 50Wx8-400, $H^+$-form, was rinsed with 10 bed volumes of DI water and dried at 125° C. The dry resin was manually ground in a mixture with dry ice. Ca. 0.5 g of ground cation exchange resin was suspended in 2.5 mL of DI water and allowed to settle for 60 min. The unsettled (colloidal) suspension was used. The anion exchange resin (Dowex-1x8) was prepared similarly but without high temperature drying.

EXAMPLE 2

Figure 3:
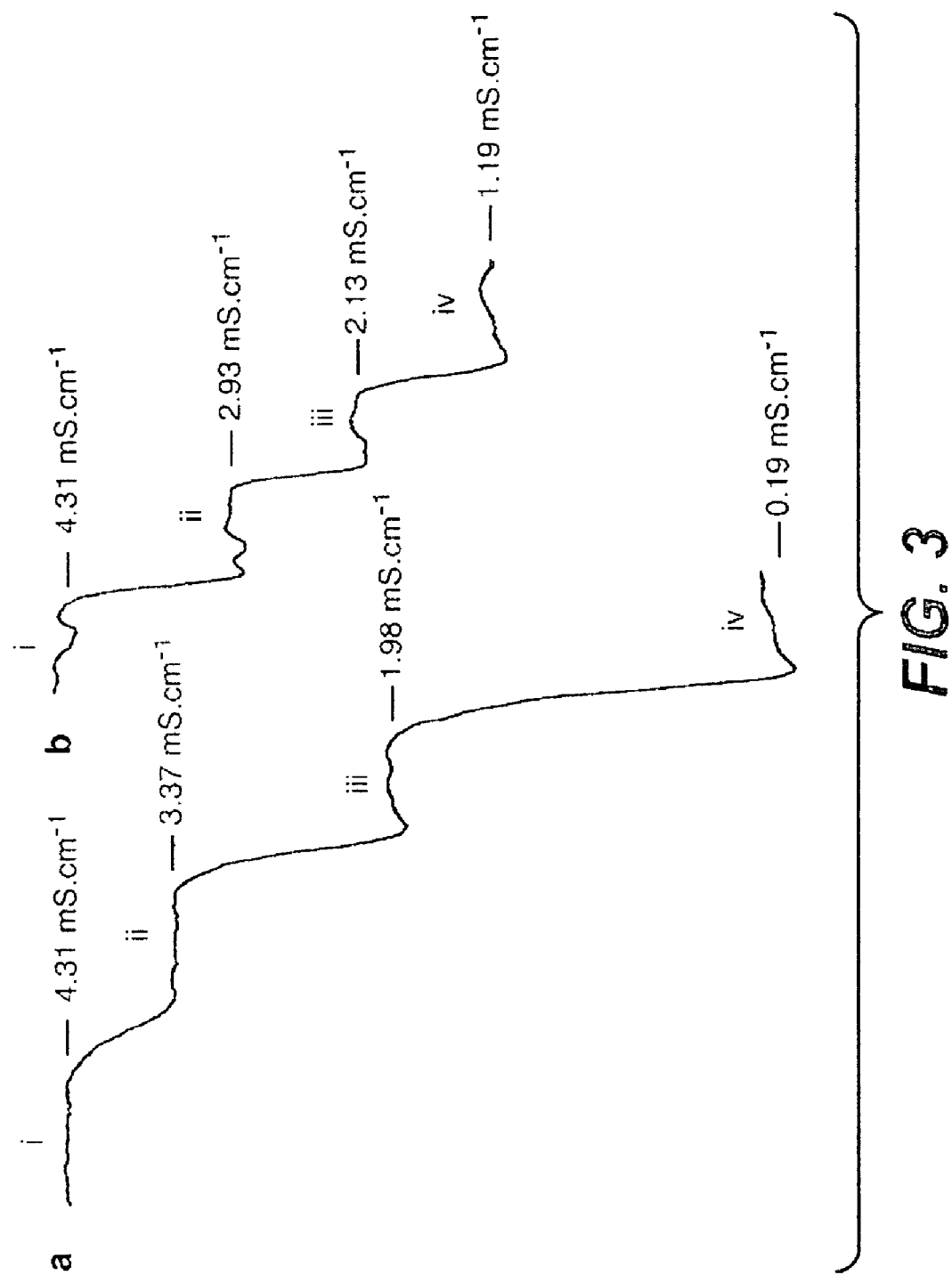
FIG. 3. The effect of (a) the width and (b) the flow rate of the eluent flow stream on ion exchange efficiency. Conditions: 10 mM HCl eluent, ion exchanger 150 mM TOAOH in butanol+ 1% Triton X-100. (a): flow rate 5 μL min$^{-1}$ (i) nonsuppressed eluent, (ii) eluent width 750 μm (iii) eluent width 500 μm, (iv) eluent width 250 μm; (b): eluent channel width 500 μm, (i) nonsuppressed eluent, (ii) flow rate 10 μL min$^{-1}$, (iii) flow rate 5 μL min$^{-1}$, (iv) flow rate 2 μL min$^{-1}$. Note that the conductivity detector output is not completely linear with the actual specific conductance over the entire region, as such we have provided individual ordinate markings in this and similar figures rather than providing a linearly calibrated axis.

FIG. 3a shows the effect of different flow rates in the experimental system of Example 1 (see FIG. 16A). Each phase was 500 μm wide. 10 mM HCl and 150 mM butanolic TOAOH were used as eluent and exchanger phases, respectively. In general, the results conform well with the computational results shown in FIG. 2; however, small leaching of the ion exchanger into the aqueous phase makes it more difficult to exactly compute the fraction exchanged as the fraction exchanged value gets higher. As predicted, the fraction exchanged increases with decreasing flow rates. The contact time in the present device with phase widths of 500 μm and flow rates of 2 μL/min is ~50 s. As predicted in FIG. 2a. a greater degree of suppression can be achieved by decreasing the width of the eluent phase. In the present experimental system, this is most easily achieved by adjustment of relative solution reservoir height s. FIG. 3b shows the effect of decreasing the width of the eluent phase from 750 μm to 500 μm to 250 μm.

EXAMPLE 3

Figure 4:
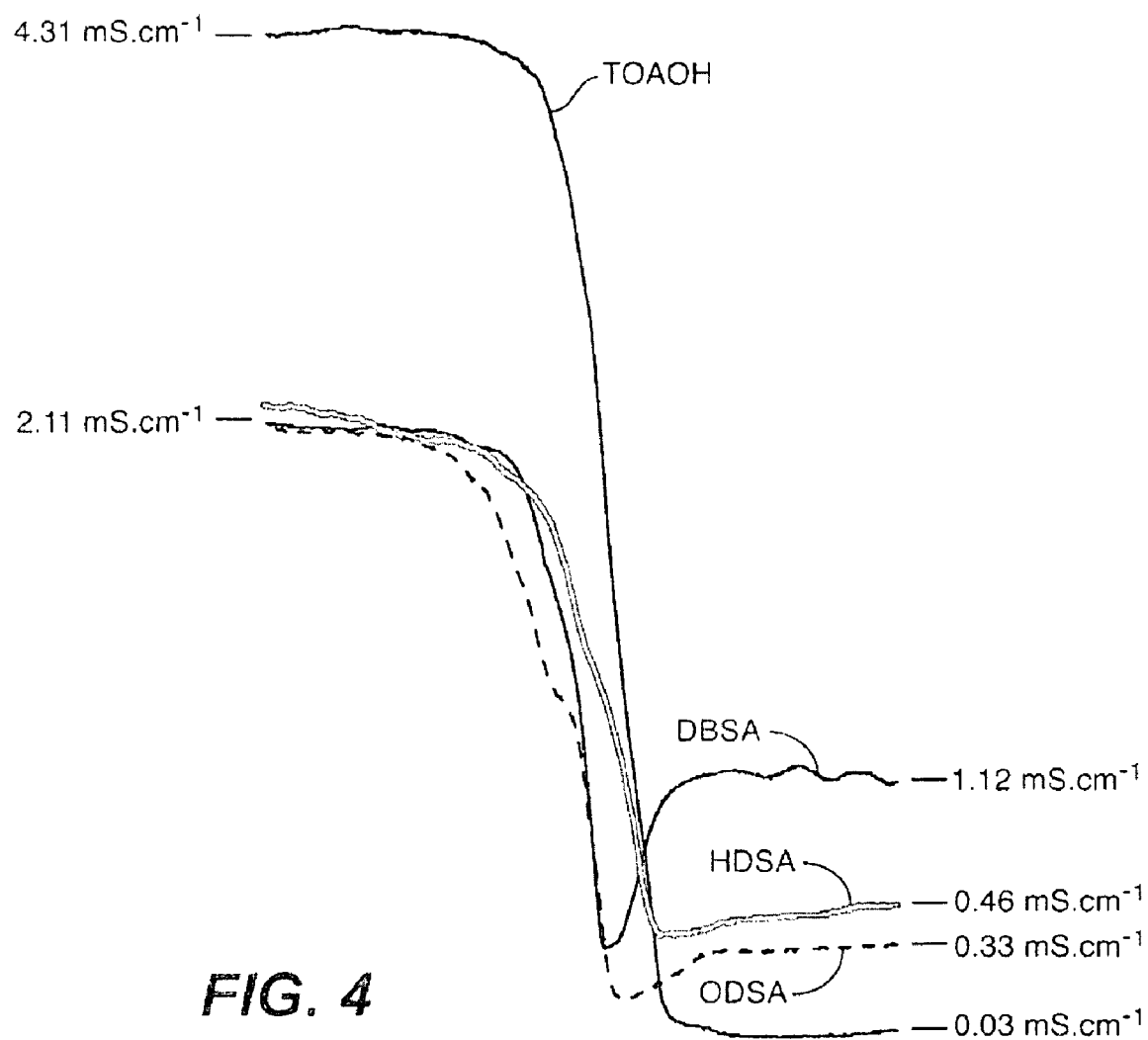
FIG. 4. Comparison of suppressed conductance values obtained with different eluent-ion exchanger combinations.

FIG. 4 shows the background conductance achieved with 10 mM HCl and 10 mM NaOH eluents, using an eluent flow rate of 2 μL/min and an eluent phase width of 250 μm. The suppressed background conductance attained with TOAOH used in conjunction with an acid eluent is much lower than that obtained with an NaOH eluent and various alkylsulfonic acid ion exchangers. The leaching of the acids into the aqueous phase (Table 1) appears to be the main limitation. (We believe that this problem can be solved by using lipophilic alkali metal complexing agents; preliminary experiments with sym-(n-decyl)dibenzo16-crown-6-oxyacetic acid, for example, showed promising results.)

EXAMPLE 4

Figure 5:
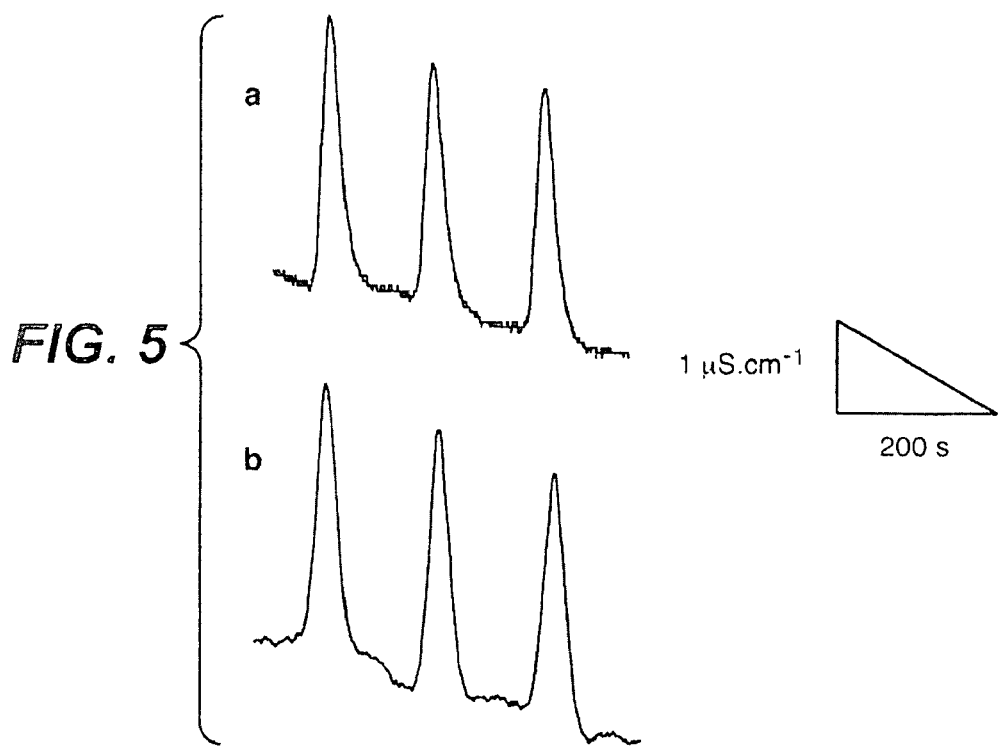
FIG. 5. Triplicate injections of 0.5 mM NaCl into an 1 mM HCl eluent phase. Conditions: injection volume: 650 nL, flow rate: 2 μL min$^{-1}$, eluent width 250 μm, (a) 15 mM TOAOH in butanol, 1% Triton X-100; (b) 1% Amberlite LA-2 in butanol containing 1% Triton X-100.

FIG. 5 shows triplicate injections of 0.5 mM NaCl into a 1 mM HCl eluent, using both 15 mM TOAOH or 1% Amberlite LA-2 as the ion exchanger. The estimated S/N=3 limit of detection (LOD) from these data is ≦0.1 mM NaCl, largely controlled by dispersion in the injector and the suppression device as well as the larger than optimum detection electrodes; the detector electronics used here are also dated.

EXAMPLE 5

Figure 6:
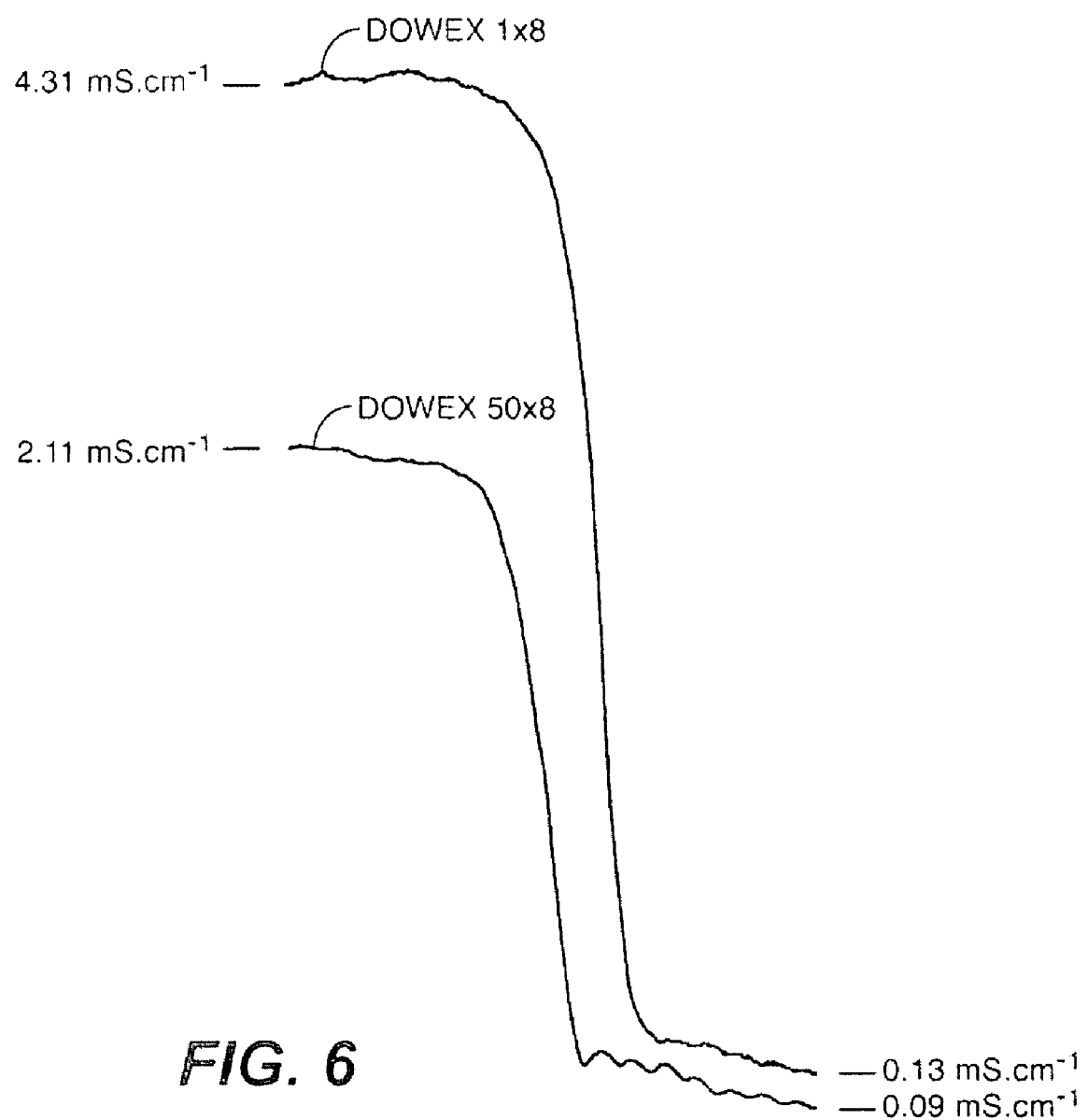
FIG. 6. Comparison of suppressed conductance values obtained with different eluent-suspended ion exchanger combinations.
Figure 8A:
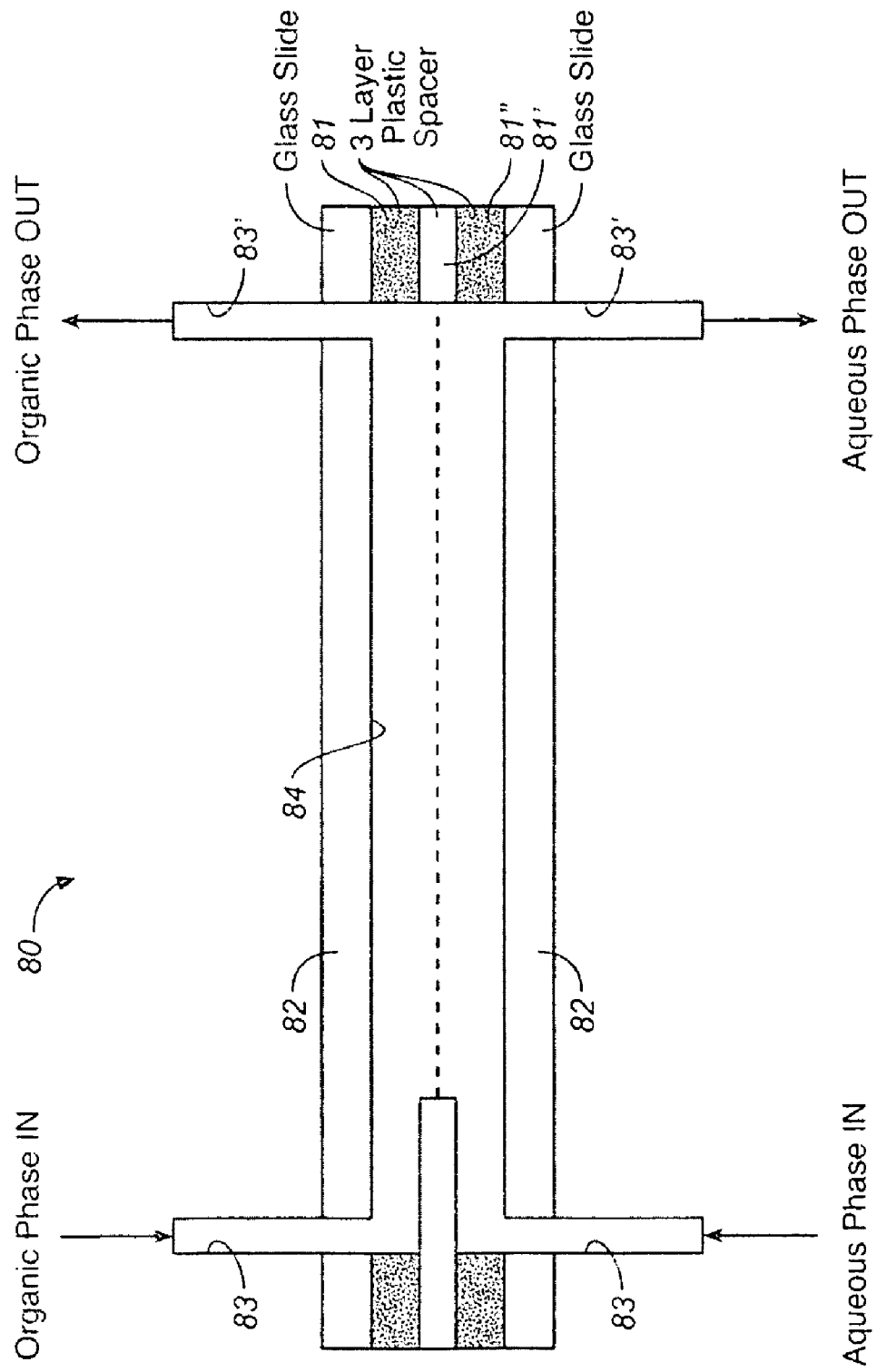
FIG. 8. The scheme of the device for continuous extraction /ion exchange in vertically stratified horizontal flows (upper part). Lower part: Process of extraction (a), ion-pair extraction (b,c) and ion exchange (d).
Figure 8B:
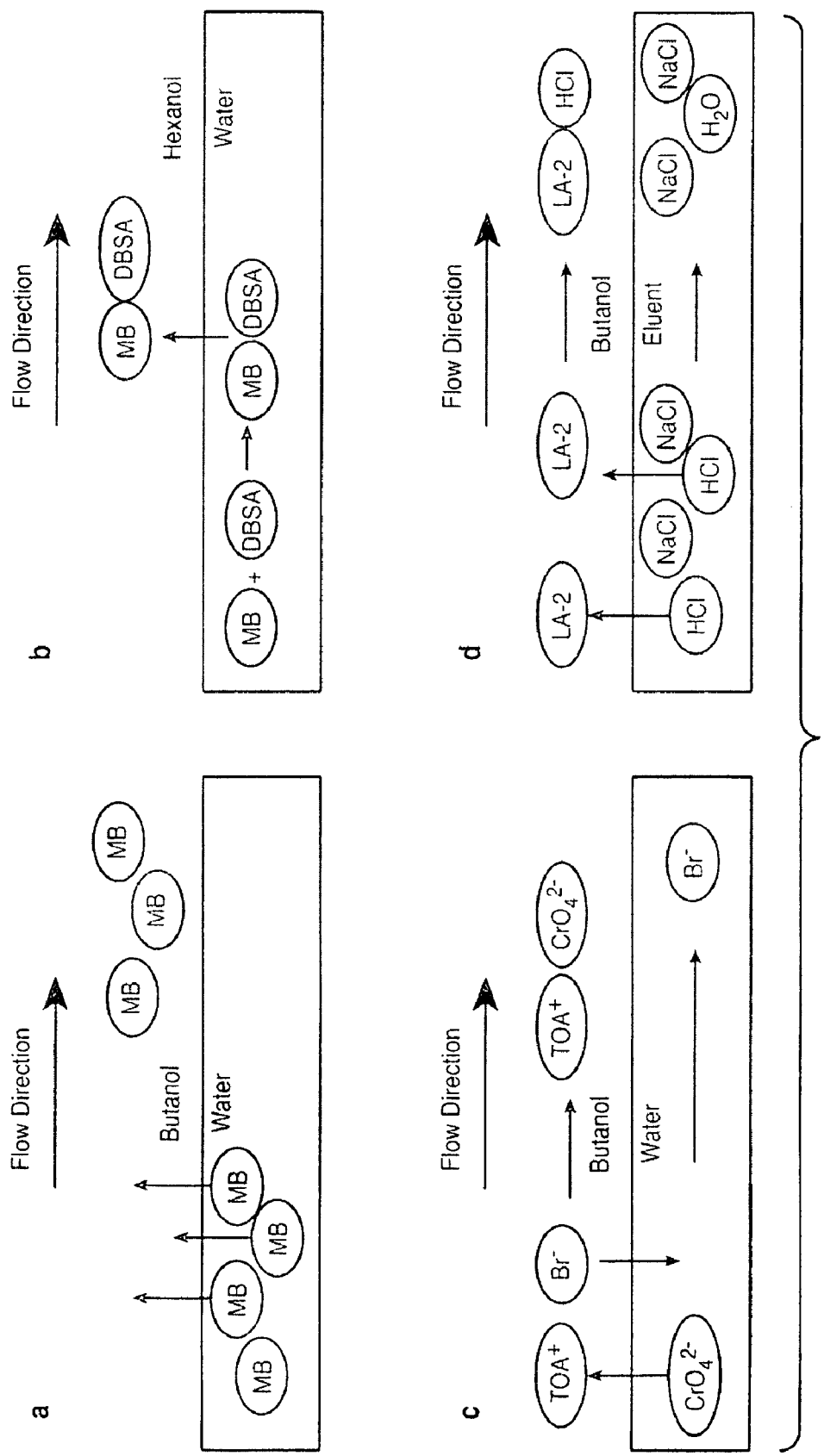

FIG. 6 shows conductivity suppression experiments with colloidal aqueous ion exchanger suspension. The efficiency is similar for anion and cation exchanger suspensions and, as such, may be predicted from an effect comparable to that observed for the TOAOH system. The residual conductance probably arises from impurities in the ion exchanger suspension generated during grinding, etc., since the suspension was not purified. Various concentrations of NaCl were injected from a sub- mM to 10 mM level in a 10 mM NaOH-Dowex 50WX8 suspension system. The high concentrations resulted in peaks exceeding 100 μS/cm in height. Similar results were achieved for the suppression of 10 mM NaOH with the anion exchanger resin suspension. One obvious benefit of using resin suspensions is that no organic solvents are involved.

EXAMPLE 6

Figure 7:
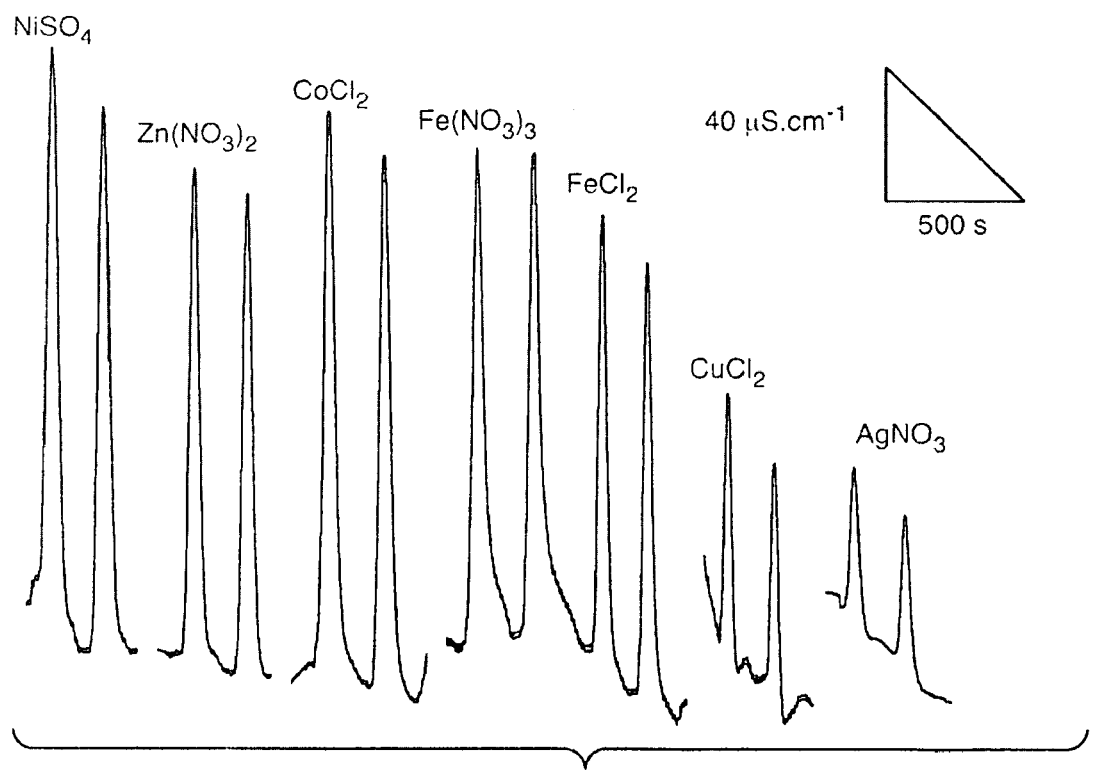
FIG. 7. Conductivity detection of various heavy metals in the system with 1% Amberlite LA-2 in butanol, 1% Triton X-100. Conditions are the same as those for FIG. 6b. 1 mM HNO$_3$ was used as eluent for silver nitrate injection.

FIG. 7 demonstrates the feasibility of conductometric detection of a range of heavy metals injected into the system with Amberlite LA-2. Note that even metals such as silver or copper can be detected, though their sensitivity is somewhat lower than the corresponding sensitivity for other metals, probably due to their complex formation with the secondary amine present in the exchanger phase. This approach can potentially have an appropriately functionalized membrane-based analog in a macrosystem.

EXAMPLE 7

This example illustrates the approach using two immiscible liquids, one onto the other.

Device. Whitesides and Stroock[25] have recently described versatile flexible methods to construct microfluidic devices 80, especially by soft lithography. We have recently described an approach to experimenting with flow in shallow planar devices using tapes/thin sheets or layers 81, 81', 81" as spacers and with binder clips to hold things together.[26] A microfluidic device was constructed from two glass slides 82 (25× 75×1 mm) and a plastic spacer. Two holes were drilled into each of the glass slides 82 at the distance of 45 mm. Inlet and outlet stainless steel tubings 83, 83' (575 μm i.d. 1.05 mm o.d.) were affixed into the holes with epoxy glue. The flow channel 84 between two glass slides 82 was formed by a plastic spacer made from three layers of materials. Black electric tape (thickness 150 μm) or Kapton tape (thickness 80 or 50 μm) and a transparency sheets (thickness 80 and 50 μm) were used as spacer materials. The final thickness of the spacer defining the channel depth could thus be varied from 150 μm to 400 μm. The approximate volume of the channel was 10 to 30 μL depending on its depth. The schematic of the device is depicted on FIG. 8 (upper part). FIGS. 8a to 8d (lower part) demonstrate the principles of several processes that can take place in this device.

Initial experiments showed that the hydraulic resistance of the device is relatively small. Even a 10 cm hydrostatic head produced flow rates much higher than that desired. The respective liquids were therefore aspirated by a peristaltic pump (Dynamax, Rainin Instrument Co. LTD, USA) from the device outlets at 20-160 μL/min. The liquids were aspirated at given flow rates from both outlets, thus the total volumetric flow rate was the sum of the individual flow rates from the outlets. The inlet liquid reservoirs were connected to the device with large bore tubing (1.25 mm) to eliminate any flow resistance. Nominally the inlet reservoirs were maintained at a hydrostatic height of 20 cm. However, the reservoir heights were adjusted to modify the thickness of the solution layers flowing horizontally through the channel.

For sample injection, an FIA injector (Lachat Instruments) was connected between the microfluidic device and the fluid reservoirs. Injections into the eluent stream were made with a loop-type valve with loop volume of 5 μL.

On-line absorbance measurements were performed with an ISCO CV[12] capillary cell detector. A 20 cm long fused silica capillary (o.d. 353 μm, i.d. 180 μm) was connected inside the outlet tubing of the microfluidic device to minimize the dispersion. The absorbance of the organic phase was measured at 656 nm (extraction of methylene blue) or 372 nm (ion-pair extraction of chromate).

Off-line experiments, e.g. the solutions from the device were collected and diluted, were measured on a HP 8453 spectrophotometer. The conductivity detection electrodes were constituted of a concentric cell consisting of an inner stainless steel tube (175 μm id, 350 μm od) and an outer stainless tube (575 μm id, 1.05 mm od) separated by a PTFE tube acting as a spacer. This assembly was placed in the exit of the channel used for the aqueous eluent phase. The electrodes were connected to a relatively early model commercial conductivity detector (Model CDM-1, Dionex Corp.). No preamplifier[14] was used and S/N was not optimized.

Chemicals, solutions. All chemicals were of reagent grade. Aqueous stock solutions of methylene blue, dodecylbenzenesulfonic acid (DBSA, Stepan Chemical, Northfield, Ill.), and potassium chromate (Mallinckrodt, St. Louis, Mich.) were prepared with deionized water and diluted to the desired concentration. Butanol (EM Science, Gibbstown, N.J.), pentanol, hexanol (Acros), benzylalcohol (Mallinckrodt, St. Louis, Mich.), hexane (EM Science, Gibbstown, N.J.) and chloroform, were used as the immiscible organic phase. Tetraoctylammonium bromide (TOABr, Sigma-Aldrich) and Amberlite LA-2 (Aldrich), a secondary amine type anion exchanger, were used without further purification. The tetraoctylammonium hydroxide was prepared as described previously. Typically, solutions were degassed by ultrasonication prior to use but reagents were not pretreated beyond this.

LITERATURE CITED

[1] Small, H.; Stevens, T. S.; Baumann, W. C. *Anal. Chem.* 1975, 47, 1801-1809.

[2] Rokhushika, S.; Qiu, Z. Y.; Hatano, H. *J. Chromatogr.* 1983, 260, 81-87.

[3] Sjögren, A.; Boring, C. B.; Dasgupta, P. K.; Alexander, J. N. IV, *Anal. Chem.* 1997, 69, 1385-1391; Boring, C. B.; Dasgupta, P. K.; Sjögren, A. *J. Chromatogr.* 1998, 804, 45-54.

[4] Dasgupta, P. K.; Bao, L. *Anal. Chem.* 1993, 65, 1003-1011; Avdalovic, N.; Pohl, C. A.; Rockin, R. D.; Stillian, J. R. *Anal Chem.* 1993, 65, 1470-75.

[5] Pyo, D.; Dasgupta, P. K.; Yengoyan, L. S. *Anal. Sci.* 1997, 13 (Suppl), 185-190.

[6] Murrihy, J. P.; Breadmore, M. C.; Tan, A.; McEnery, M. Alderman, J.; O'Mthuna, C.; O'Neill, A. P.; O'Brien, P.; Avdalovic, N.; Haddad, P. R.; Glennon, J. D. *J. Chromatogr.* 2001, 924, 233-238.

[7] Kutter, J. P. *Trends Anal. Chem.* 2000, 19, 352-363.

[8] Kang, Q.; Golubovic, N. C.; Pinto, N. G.; Henderson, H. T. *Chem. Eng. Sci.* 2001, 56, 3409-3420.

[9] Yager, P.; Weigl, B. H.; Brody, J. P.; Holl, M. R. U.S. Pat. No. 5,716,852, February, 1998.

[10] Weigl, B. H.; Yager, P. *Science* 1999, 346-347.

[11] Kamholz, A. E.; E. A. Schilling, Yager, P. *Biophys. J.* 2001, 80, 1967-1972.

[12] Kamholz, A. E.; Weigl, B. H.; Finlayson, B. A.; Yager, P. *Anal. Chem.* 1999, 71, 5340-5347.

[13] Hatch, A.; Kamholz, A. E.; Hawkins, K. R.; Munson, M. S.; Schilling, E. A.; Weigly, B. H.; Yeager, P. *Nature Biotechnol.* 2001, 19, 461-465.

[14] Yager, P.; Brody, J. P.; Holl, M. R.; Forster, F. K.; Galambos, P. C. U.S. Pat. No. 5,932,100.

[15] www.micronics.net

[16] Giddings, J. C. U.S. Pat. No. 4,147,621, April 1979; U.S. Pat. No. 4,737,268, April, 1988; U.S. Pat. No. 4,894,146, January 1990; U.S. Pat. No. 5,039,426, August 1991.

[17] Sato, K.; Tokeshi, M.; Kitamori, T.; Sawada, T. *Anal Sci.* 1999, 15, 641-645.

[18] Tokeshhi, M.; Minagawa, T.; Kitamori, T. *J. Chromatogr. A.* 2000, 894, 19-23.

[19] Sato, K.; Tokeshi, M.; Sawada, T.; Kitamori, T. *Anal. Sci.* 2000, 16, 455-456.

[20] Surmeian, M.; Hibara, A.; Slyadnev, M.; Uchiyama, K.; Hisamoto, H.; Kitamori, T. *Anal. Lett.* 2001, 34, 1421-1429.

[21] Tokeshi, M.; Minagawa, T.; Kitamori, T. *Anal. Chem.* 2000, 72, 1711-1714.

[22] Hibara, A.; Tokeshi, M.; Uchiyama, K.; Hisamoto, H.; Kitamori, T. *Anal. Sci,* 2001, 17, 89-93.

[23] Hisamoto, H.; Horiuchi, T.; Tokeshi, M.; Hibra, A.; Kitamori, T. *Anal. Chem.* 2001, 73, 1382-1386.

[24] Hisamoto, H.; Horiuchi, T.; Uchiyama, K.; Tokeshi, M.; Hibara, A.; Kitamori, T. *Anal Chem.* 2001, 73, 5551-5556.

[25] Whitesides, G. M.; Stroock, A. D. *Physics Today,* 2001, 54, 42-46.

[26] Dasgupta, P. K.; Surowiec, K.; Berg. J. *Anal Chem.* 2002, 74, 208A-213A.

[27] Dasgupta, P. K. *Anal. Chem.* 1984, 56, 96-103.

[28] Srinivasan, K.; Saini, S.; Avdalovic, N. Recent Advances in Continuously Regenerated Suppressor Devices. Abstract 136, 2001 Pittsburgh Conference, New Orleans, La., March, 2001.

[29] Gjerde, D. T.; Benson, J. V. U.S. Pat. No. 5,149,661, May, 1989; Gjerde, D. T., Benson, J. V. *Anal Chem* 1990, 62, 12-615; Jandik, P.; Li, J. B.; Jones, W. R.; Gjerde, D. T. *Chromatographia,* 1990, 30, 509-517; Jackson, P. E.; Jandik, P.; Li, J.; Krol, J.; Bondoux, G.; Gjerde, D. T. *J. Chromatogr.* 1991, 546, 189-198; Gjerde, D. T.; Cox, D. J.; Jandik, P.; Li, J. B. *J. Chromatogr.* 1991, 546, 151-158.

What is claimed is:

1. A method for treating a liquid sample stream, including a first analyte species ion and matrix ion species of opposite charge to said first analyte ion species, and for detecting said first analyte in the liquid sample stream, said method comprising flowing said sample stream from an inlet in a flow-through treatment channel to a sample stream outlet thereof, flowing a carrier liquid stream including a matrix ion species capture material through said flow-through channel to a carrier stream outlet thereof for removing said matrix ion species away from said first analyte ion species, said sample stream and carrier liquid stream flowing substantially parallel to each other in said treatment channel and forming a liquid interface between them, said matrix ion species in said sample stream diffusing through said interface to contact and become bound by said capture material in said carrier liquid by forming a salt or complex or by ion exchange so that the concentration of said matrix ion species at said outlet is at a substantially lower concentration than at said inlet, transporting the sample stream, but not the carrier stream, from said sample stream outlet, in a fluid conduit to a detector, and detecting said first analyte ion species in said sample stream by said detector.

2. The method of claim 1 in which no substantial amount of said capture material in said carrier liquid stream flows into said sample stream in said treatment channel.

3. The method of claim 1, in which said sample stream comprises at least a second analyte ion species, said method further comprises separating said first and second analyte ion species in said sample steam prior to flowing said sample stream to the treatment channel inlet.

4. The method of claim 1 in which said liquid sample stream is aqueous, said ion exchange material is in liquid form, and said carrier liquid stream is an organic liquid solvent for said ion exchange material.

5. The method of claim 1 in which said ion exchange material comprises solid ion exchange particles suspended in said carrier liquid stream.

6. The method of claim 1 in which said carrier liquid stream is substantially immiscible in said aqueous liquid stream.

7. The method of claim 1 in which said carrier liquid stream is substantially miscible in said aqueous liquid stream.

8. The method of claim 3 in which said matrix ion species is suppressed on exiting said treatment channel.

9. A method for treating a liquid sample stream including at least one analyte species ion and matrix ion species of opposite charge to said one analyte ion species, said method comprising flowing said sample stream from an inlet in a flow-through treatment channel to an outlet thereof, and flowing a carrier liquid stream including a matrix ion species capture material through said flow-through channel for removing said matrix ion species away from said at least one analyte ion species, said sample stream and carrier liquid stream flowing substantially parallel to each other in said treatment channel and forming a liquid interface between them, said matrix ion species in said sample stream diffusing through said interface to contact and become bound by said capture material in said carrier liquid so that the concentration of said matrix ion species at said outlet is at a substantially lower concentration than at said inlet, in which said capture material binds said matrix ion species by forming a salt or complex.

10. The method of claim 1 in which said sample stream and carrier liquid stream flow under substantially laminar flow conditions.

11. The method of claim 1 performed in the absence of an applied electric current.

* * * * *

UNITED STATES PATENT AND TRADEMARK OFFICE
CERTIFICATE OF CORRECTION

PATENT NO. : 7,582,482 B2
APPLICATION NO. : 10/653032
DATED : September 1, 2009
INVENTOR(S) : Purnendu K. Dasgupta, Petr Kuban and Jordan M. Berg It is certified that error appears in the above-identified patent and that said Letters Patent is hereby corrected as shown below:

Title Page, Item (75) should read:

--(75) Inventors: Purnendu K. Dasgupta, Lubbock, TX (US); Petr Kuban, Lubbock, TX (US); Jordan M. Berg, Lubbock, TX (US)--

Column 24, Lines 22 - 26; Claim 3 should read:

--3. The method of claim 1, in which said sample stream comprises at least a second analyte ion species, said method further comprising separating said first and second analyte ion species in said sample steam prior to flowing said sample stream to the treatment channel inlet.--

Signed and Sealed this

Tenth Day of November, 2009

David J. Kappos
*Director of the United States Patent and Trademark Office*